US011896653B2

(12) United States Patent
Serda et al.

(10) Patent No.: US 11,896,653 B2
(45) Date of Patent: Feb. 13, 2024

(54) SILICIFIED CELL REPLICAS, METHODS OF MAKING, AND METHODS OF USING

(71) Applicant: UNM Rainforest Innovations, Albuquerque, NM (US)

(72) Inventors: Rita E. Serda, Albuquerque, NM (US); C. Jeffrey Brinker, Albuquerque, NM (US); Jacob Ongudi Agola, Albuquerque, NM (US); Jimin Guo, Albuquerque, NM (US); Sarah Adams, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 610 days.

(21) Appl. No.: 16/647,245

(22) PCT Filed: Sep. 13, 2018

(86) PCT No.: PCT/US2018/050831

§ 371 (c)(1),
(2) Date: Mar. 13, 2020

(87) PCT Pub. No.: WO2019/055620

PCT Pub. Date: Mar. 21, 2019

(65) Prior Publication Data

US 2020/0276286 A1 Sep. 3, 2020

Related U.S. Application Data

(60) Provisional application No. 62/557,934, filed on Sep. 13, 2017.

(51) Int. Cl.
*A61K 39/00* (2006.01)
*A61K 39/39* (2006.01)

(52) U.S. Cl.
CPC .......... *A61K 39/0011* (2013.01); *A61K 39/39* (2013.01); *A61K 2039/55594* (2013.01); *A61K 2039/6006* (2013.01)

(58) Field of Classification Search
None
See application file for complete search history.

(56) References Cited

U.S. PATENT DOCUMENTS

| | | | |
|---|---|---|---|
| 6,294,177 B1 | 9/2001 | Fattom | |
| 2004/0191229 A1 | 9/2004 | Link, Jr. et al. | |
| 2009/0181078 A1 | 7/2009 | Reed et al. | |
| 2014/0363872 A1 | 12/2014 | Jaroch et al. | |

FOREIGN PATENT DOCUMENTS

WO WO 2014121132 A1 8/2014

OTHER PUBLICATIONS

Cancer Genome Atlas Research, Integrated genomic analyses of ovarian carcinoma. *Nature* 474, 609-615 (2011).

Chiang et al., Whole Tumor Antigen Vaccines: Where Are We? *Vaccines* (*Basel*) 3, 344-372 (2015).

Hamm et al., Architecture and material properties of diatom shells provide effective mechanical protection. *Nature* 421, 841-843 (2003).

Hanna, Immunotherapy with autologous tumor cell vaccines for treatment of occult disease in early stage colon cancer. *Hum Vaccin Immunother* 8, 1156-1160 (2012).

International Search Report and Written Opinion for PCT/US2018/050831 dated Dec. 20, 2018, 6 pages.

International Preliminary Report on Patentability for PCT/US2018/050831 dated Mar. 17, 2020, 5 pages.

Kaehr et al., Cellular complexity captured in durable silica biocomposites. *Proc Natl Acad Sci U S A* 109, 17336-17341 (2012).

Kurtz et al., Current status of autologous breast tumor cell-based vaccines. *Expert Rev Vaccines* 13, 1439-1445 (2014).

Lou et al., Silica bioreplication preserves three-dimensional spheroid structures of human pluripotent stem cells and HepG2 cells. *Sci Rep* 5, 13635 (2015).

Radford et al., A recombinant *E. coli* vaccine to promote MHC class I-dependent antigen presentation: application to cancer immunotherapy. *Gene Ther* 9, 1455-1463 (2002).

Serda et al., The association of silicon microparticles with endothelial cells in drug delivery to the vasculature. *Biomaterials* 30, 2440-2448 (2009).

Srivatsan et al., Allogeneic tumor cell vaccines: the promise and limitations in clinical trials. *Hum Vaccin Immunother* 10, 52-63 (2014).

Sumper et al., Silica biomineralization in diatoms: the model organism Thalassiosira pseudonana. *Chembiochem* 9, 1187-1194 (2008).

Utaisincharoen et al., Kinetic studies of the production of nitric oxide (NO) and tumour necrosis factor-alpha (TNF-alpha) in macrophages stimulated with Burkholderia pseudomallei endotoxin, *Clin Exp Immunol* 122, 324-329 (2000).

Vaccelelli et al., Trial watch: FDA-approved Toll-like receptor agonists for cancer therapy. *Oncoimmunology* 1, 894-907 (2012).

Walker et al., Geobiology of a microbial endolithic community in the Yellowstone geothermal environment. *Nature* 434, 1011-1014 (2005).

Wang et al., Hydrated silica exterior produced by biomimetic silicification confers viral vaccine heat-resistance. *ACS Nano* 9, 799-808 (2015).

Wang et al., Immunogenic effects of chemotherapy-induced tumor cell death. *Genes Diseases* 5, 194-203 (2018).

Kim et al., Intra-mitochondrial biomineralization for including apoptosis of cancer cells, Chem. Sci., 2018, 9, 2474; DOI: 10.1039/c7sc05189a (Year: 2018).

Serrano et al., Liposomal vaccine formulations as prophylactic agents: design considerations for modern vaccines; J Nanobiotechnol (2017) 15:83; DOI 10.1186/s1295-017-0319-9 (Year: 2017).

International Patent Application No. PCT/US2021/063386, filed Dec. 14, 2021, International Preliminary Report on Patentability, dated Jun. 13, 2023, 7 pages.

*Primary Examiner* — Brian Gangle
(74) *Attorney, Agent, or Firm* — Mueting Raasch Group

(57) ABSTRACT

A silicified cell replica includes a silicified cell or a silicified subcellular fragment. The silicified cell replica may be used to induce an immunological response, treat a bacterial infection, or treat a patient with cancer.

20 Claims, 13 Drawing Sheets

Specification includes a Sequence Listing.

A

B

D

E

F: 4% parafomaldehyde; Si: silicified in TMOS/HCl for indicated amount of time (hours); D: dedydrated following Si

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: synthetic construct

<400> SEQUENCE: 1
```

-continued

```
Ser Ile Ile Asn Phe Glu Lys Leu
1               5
```

SILICIFIED CELL REPLICAS, METHODS OF MAKING, AND METHODS OF USING

CROSS-REFERENCE TO RELATED APPLICATION

This application is the § 371 U.S. National Stage of International Application No. PCT/US2018/050831, filed Sep. 13, 2018, which claims the benefit of U.S. Provisional Application No. 62/557,934, filed Sep. 13, 2017, each of which is incorporated herein by reference in its entirety.

GOVERNMENT FUNDING

This invention was made with government support under contract DE-NA0003525 awarded by the United States Department of Energy/National Nuclear Security Administration. The government has certain rights in the invention.

SEQUENCE LISTING

This application contains a Sequence Listing electronically submitted to the United States Patent and Trademark Office via Patent Center as an ASCII text file entitled "0310_000123US01_ST25" having a size of 522 bytes and created on Jun. 26, 2023. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes, in one aspect, a composition that includes a silicified cell or a silicified subcellular fragment. In some cases, the silicified subcellular fragment can include a silicified cell-derived body or a silicified vesicle. In some cases, the composition can be formulated as a pharmaceutical composition such as, for example, a vaccine.

In some embodiments, the silicified cell can be a silicified bacterial cell.

In some embodiments, the silicified cell can be a silicified tumor cell.

In some embodiments, the silicified cell can be a cell obtained from a spheroid or organoid.

In some embodiments, the silicified cell can include surface-modified siloxane. In some of these embodiments, the surface-modified siloxane can include a pathogen-associated molecular pattern (PAMP) or danger-associated molecular molecule (DAMP) adhered to the surface. In other embodiments, the surface-modified siloxane can include a molecule that promotes internalization by antigen presenting cells. In still other embodiments, the silicified cell is further modified with a secondary silane.

In another aspect, this disclosure describes a method of inducing an immune response against an antigen. Generally, the method includes obtaining a cell that expresses the antigen, silicifying the cell, and administering the silicified cell to a subject in an amount effective to induce the subject to produce an immune response directed against the antigen.

In some embodiments, the composition administered to the subject further includes an effective amount of a pharmaceutically acceptable adjuvant.

In some embodiments, the silicified cell is a bacterium.

In some embodiments, the silicified cell is a tumor cell.

In another aspect, this disclosure describes a method for treating a subject having, or at risk of having, a bacterial infection. Generally, the method includes obtaining a bacterial cell that the subject is, or is at risk, of being infected by, silicifying the bacterial cell, and administering the silicified bacterial cell to the subject in an amount effective to ameliorate at least one symptom or clinical sign of infection by the bacterial cell.

In some embodiments, the bacterial cell is obtained from the subject.

In some embodiments, the composition administered to the subject further includes an effective amount of a pharmaceutically acceptable adjuvant.

In another aspect, this disclosure describes a method for treating a subject having, or at risk of having, tumor. Generally, the method includes obtaining a tumor cell that the subject has or is at risk of having, silicifying the tumor cell, and administering the silicified tumor cell to the subject in an amount effective to ameliorate at least one symptom or clinical sign of having the tumor.

In some embodiments, the tumor cell is obtained from the subject. In some of these embodiments, the tumor cell is obtained from fluid from the subject's peritoneal cavity.

In some embodiments, the composition administered to the subject further includes an effective amount of a pharmaceutically acceptable adjuvant.

The above summary is not intended to describe each disclosed embodiment or every implementation of the present invention. The description that follows more particularly exemplifies illustrative embodiments. In several places throughout the application, guidance is provided through lists of examples, and which examples can be used in various combinations. In each instance, the recited list serves only as a representative group and should not be interpreted as an exclusive list.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

This disclosure describes a novel approach for the development of vaccines using silicified cell replicas, also known as siloxane cell replicas, that are structurally intact and resistant to extreme environmental conditions. Silicified bacterial cell replicas are immunologically active and able to harness and guide immune responses, addressing the global need for versatile vaccines. The use of silicified cell replicas—or silicified cell fragments—can, for example, present a tumor antigen to antigen presenting dendritic cells in a way that overcomes tolerance mechanisms that suppress cell-mediated immune responses to cancer.

This disclosure describes using cell silicification as a method of primary or secondary fixation. Silicification not only preserves cellular architecture and renders cells stable for storage following dehydration, but also imparts novel properties, such as enhanced surface absorption. The use of silicified cell replicas presents an opportunity to engineer bacteria or other cell type with specific antigens to modulate immune responses generated through vaccination.

The majority of clinically available vaccines contain harmless versions of microbes that stimulate immune responses to antigens present in the microbes. This disclosure demonstrates that biomineralization of model Gram-negative bacteria, which naturally express danger signals (e.g. lipopolysaccharide, LPS) remain immunogenic and stable during dehydration. When transformed with the model antigen ovalbumin, the siloxane bacterial cell replicas elicited strong antigen-specific immune responses. This disclosure demonstrates antigen presenting cell (APC) uptake and intracellular trafficking of siloxane bacterial cell replicas, stimulated production of tumor necrosis factor alpha (TNF-α) and reactive oxygen species (ROS) in APC, and processing and presentation of a model protein by bone marrow-derived dendritic cells (BMDC). The disclosure further demonstrates silicification of cancer cells and the use of siloxane cancer cells or cancer cell fragments as personalized cancer vaccines. Further modification of the cell surface with immunogenic molecules, such as pathogen-associated molecular patterns (e.g. LPS, monophosphoryl lipid A (MPL), CpG, lectins, etc.) yields pathogen mimic cancer cells, transforming cancer cells into immunogenic cancer vaccines.

Silicification and Characterization of Gram Negative Bacterial Cells

Figure 1:
FIG. 1. Characterization of biomineralized (also referred to as "silicified") bacteria. (A) Schematic illustration of the fixation and silicification of bacteria. (B) TEM and elemental mapping images of fixed bacteria (B1), TEM and elemental mapping images of fixed and 72-hour silicified bacteria (B2), scale bar=1 μm. (C) Silica content of bacteria following different silicification times. (D) SEM images of fixed bacteria (D1) and SEM images of fixed and 72-hour silicified bacteria (D2), scale bar=2 μm. (E) SEM images of fixed bacteria (E1) and SEM images of fixed and silicified 72-hour bacteria (E2), scale bar=500 nm.
Figure 1:
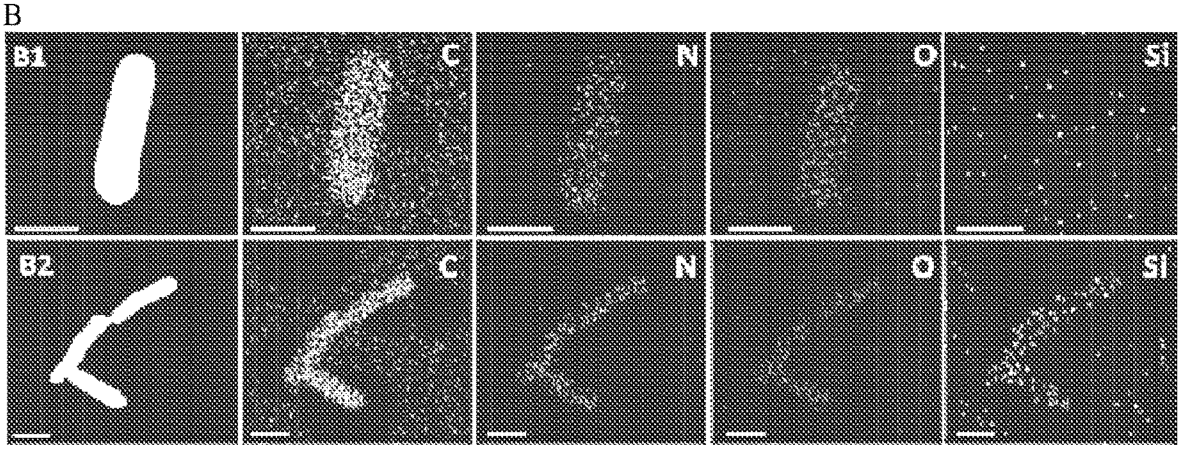
Figure 1:
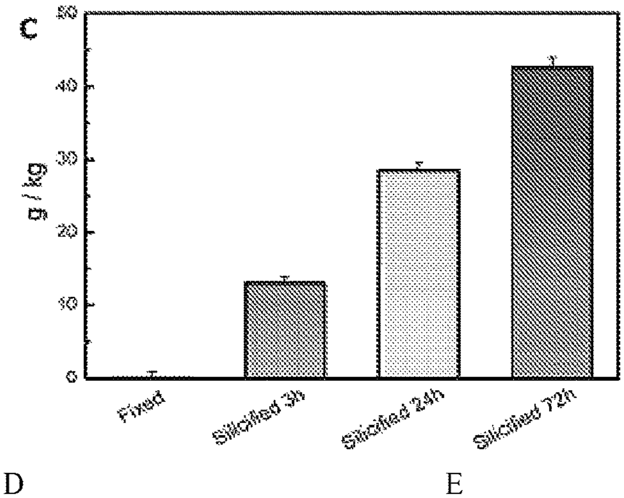
Figure 1:
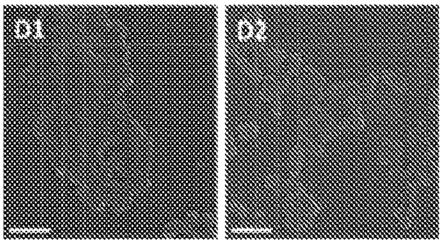
Figure 1:
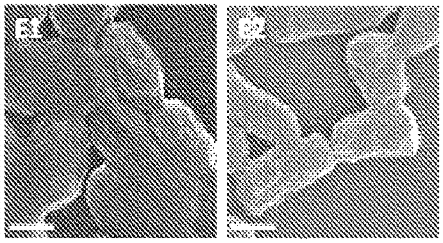
Figure 6:
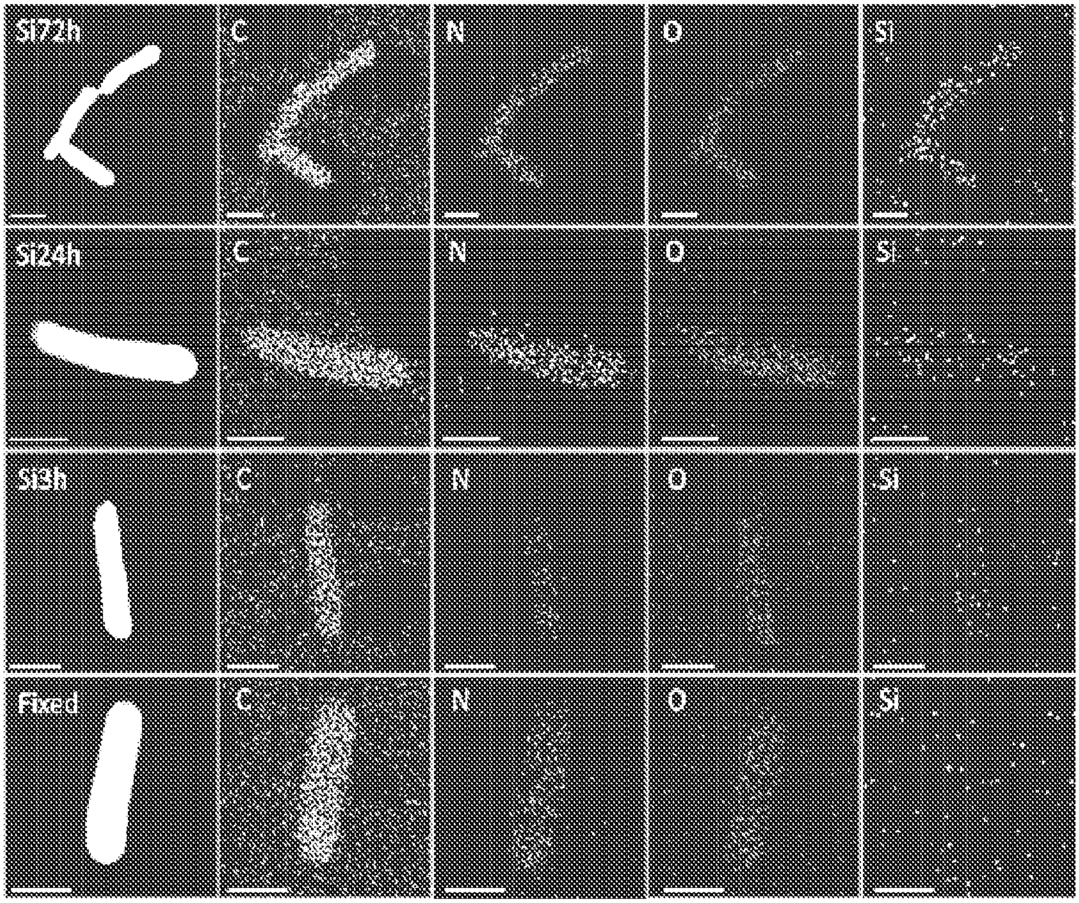
FIG. 6. Threshold for silicon detection by EDS. TEM and elemental mapping images of fixed bacteria, fixed and silicified 3-hour bacteria (Si3h), fixed and silicified 24-hour bacteria (Si24h), and fixed and silicified 72-hour bacteria (Si72h), scale bar=1 m.

Silicified bacteria were prepared by fixation and silicification, the later using a solution containing 100 mM TMOS, 154 mM NaCl, and 1.0 mM HCl (pH 3) for three hours, 24 hours, or 72 hours at room temperature (FIG. 1A). In this silicification process, silicic acid ($Si(OH)_4$) is deposited and condensed onto fixed biological interfaces under mild acidic conditions (pH 3.0), which preserves the dimensional features of the cell, including macro-structures to nano-structures. To demonstrate the silicification process, the fixed and silicified bacteria were characterized by transmission electron microscope (TEM) and elemental mapping, inductively coupled plasma-optical emission spectrometer (ICP-OES), and scanning electron microscopy (SEM). The TEM and elemental mapping images (FIG. 1B and FIG. 6) showed that there were significant Si signals after the silicification process, confirming successful silica formation. To further confirm cell silicification, ICP-OES was used to measure the Si content of silicified bacteria following different silicification times (FIG. 1C). After three hours and 24 hours silicification, there were 12.98 g/kg and 28.51 g/kg Si coated onto fixed bacteria, respectively. The continuing silicification (48 total hours) only generated ~14 g/kg Si increase, indicating that the silicification process is a biomolecular surface-directed silica assembly process and that the thickness of silica layer can be controlled by the silicification time. The morphology of the silicified bacteria was investigated by SEM with fixed bacteria as a comparison (FIG. 1D). Fixed bacteria were highly collapsed and aggregated under the high vacuum SEM imaging conditions, while the silicified bacteria maintained their original rod shape. The magnified SEM images in FIG. 1E further show that the flat morphology of fixed bacteria indicating the loss of morphology details. After silicification, surface morphology of silicified bacteria is preserved.

Internalization of Siloxane Bacterial Cell Replicas by Antigen Presenting Cells (APC)

Figure 2:
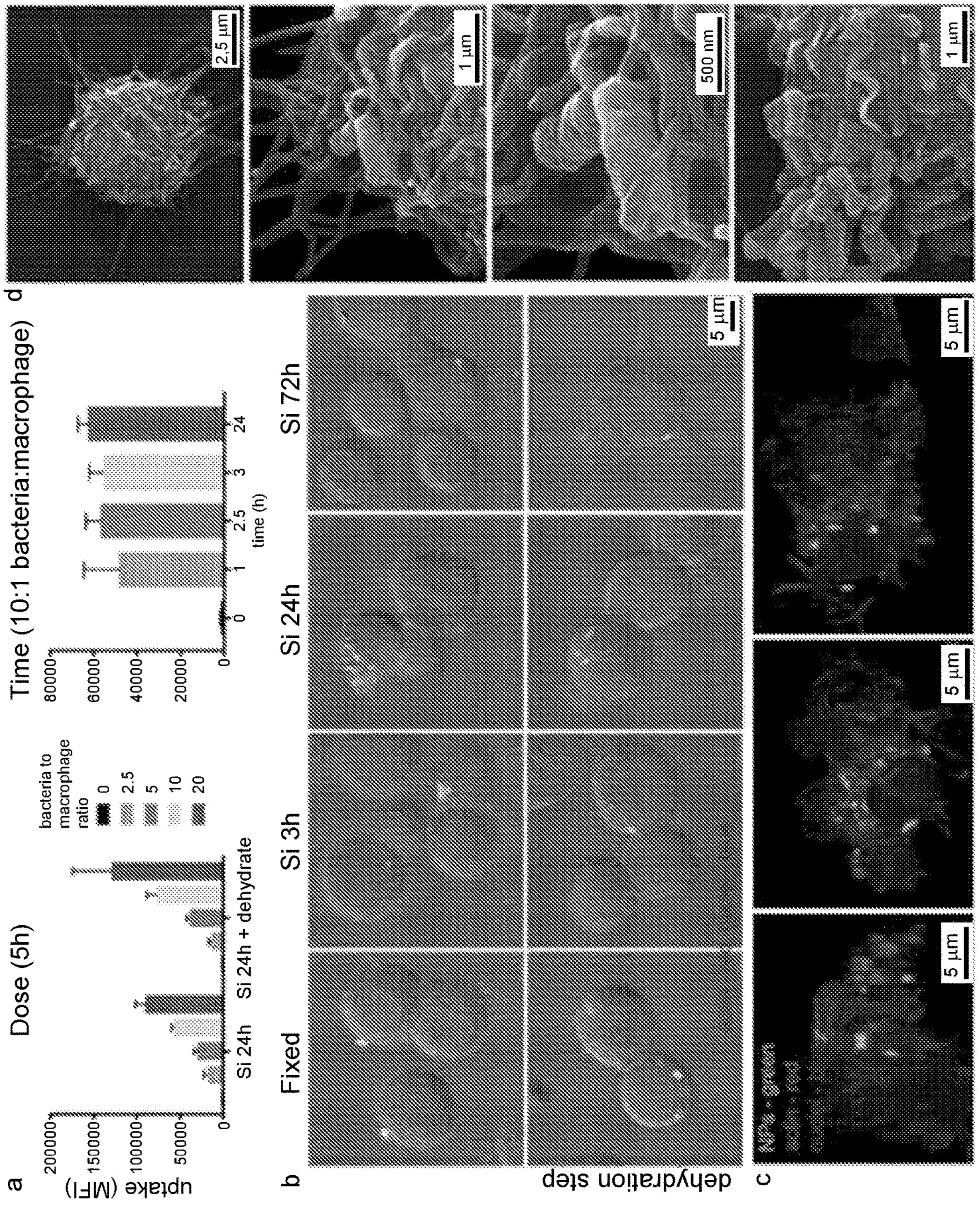
FIG. 2. Phagocytosis of silicified GFP-*Salmonella typhimurium* LT2. (A) Flow cytometry analysis of the mean fluorescent intensity (MFI) of RAW macrophages following incubation with increasing concentrations of GFP-*Salmonella typhimurium*. Bacteria were fixed, silicified, and an aliquot was dehydrated prior to adding to cells. Time-dependent uptake of fixed and 24-hour-silicified bacteria at a ratio of 10 bacteria to every RAW cell. (B) Merged confocal fluorescent and DIC micrographs of phalloidin (red, actin) and DAPI (blue, nuclei) labeled RAW cells following 1.5-hour co-culture with fixed or silicified (Si 3h is bacteria silicified for the indicated duration) bacteria at a ratio of 10 bacteria to every RAW cell. (C) 3D fluorescent micrograph showing bacteria (green) surrounded by a rings of actin (actin, red; nuclei, blue). (D) Pseudo-colored scanning electron micrographs show silicified bacteria (yellow) on the surface of RAW 264.7 macrophages (turquoise) with the first images showing the same cell at increasing magnification (3000×, 30,000×, 50,000×, 60,000×) one hour after introducing bacteria to the RAW cell culture.
Figure 9:
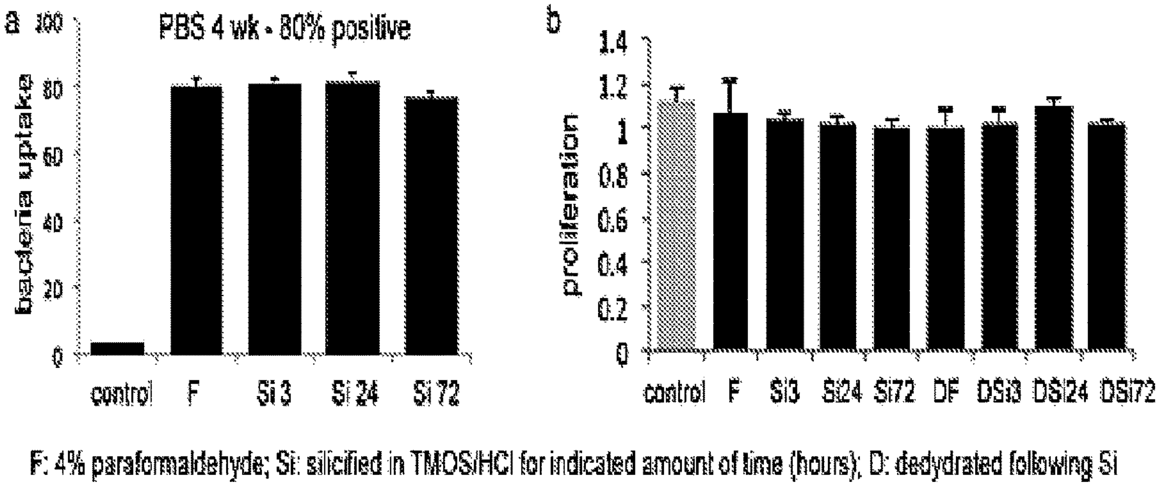
FIG. 9. Proliferation of RAW cells in the presence of silicified GFP-*Salmonella typhimurium* LT2. (A) Following four weeks of storage at 4° C., fixed (F) or fixed/silicified (Si) bacteria were added to RAW cells and cellular internalization was measured 24 hours later using flow cytometry to detect the GFP signal originating from internalized bacteria. (B) Following four weeks of storage at 4° C., either in PBS or dehydrated (D), fixed (F) or fixed/silicified (Si) bacteria were added to RAW cells and cellular proliferation was measured 24 hours later using ALAMARBLUE (Trek Diagnostic Systems, Oakwood Village, Ohio) reagent and a plate reader to detect absorbance at 570 and 600 nm.

This study evaluated the impact of fixation (protein cross-linking) and biomineralization (silification) of antigen transformed bacterial cells on immune cell responses using murine RAW 264.7 macrophage-like cells and bone marrow-derived dendritic cells. The act of cellular transformation on immune cell internalization of bacteria was evaluated in macrophages at various APC to bacterial cell ratios ranging from 0-20 GFP-*Salmonella typhimurium* bacterium to each macrophage cell. The number of bacteria internalized after five hours increased as the concentration of bacteria was increased, with similar trends observed for control and dehydrated/rehydrated bacteria that were silicified for 24 hours (FIG. 2A, left). Further, the duration of silicification did not impact uptake by macrophages (FIG. 9A). When the concentration of bacteria was held constant, the number of bacteria associated with macrophages was not significantly increased after the first hour (incubations ranged from 1-24 hours, FIG. 2A, right). Following a 24-hour exposure of RAW cells to fixed, silicified, or dehydrated GFP-*S. enterica* serovar *Typhimurium* LT2 bacterium, cellular proliferation was similar to that of untreated cells (FIG. 9B).

Figure 8:
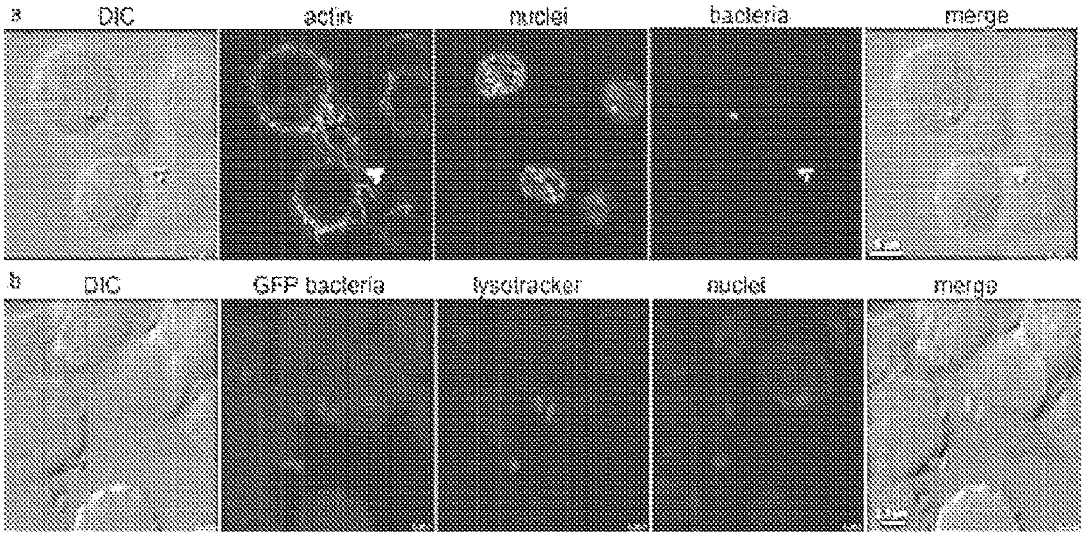
FIG. 8. Phagocytosis and intracellular localization of silicified GFP-*Salmonella typhimurium* LT2. (A) Individual (grayscale) and merged (color) confocal fluorescent and DIC micrographs of phalloidin (actin; red) and DAPI (nuclei, blue) labeled RAW cells following 1.5-hour co-culture with bacteria (GFP; green) at a ratio of 10 bacteria to every RAW cell. (B) Single fluorophore and merged confocal DIC illumination and fluorescent images of fixed bacteria and their co-localization with LYSOTRACKER Red DND-99 (Molecular Probes, Inc., Eugene, Oreg.) in RAW macrophages.

The influence of duration of silicification on bacterial cell association with macrophages was examined using confocal microscopy. Phalloidin staining of the actin cytoskeleton was used to mark the cell periphery and nuclei were visualized using DAPI. Following a 1.5-hour incubation of GFP transformed *Salmonella typhimurium* and RAW macrophages (10:1 respectively), cells were fixed and merged fluorescent and DIC images were acquired (FIG. 2B; unmerged images are included in FIG. 8A). All fixed and silicified cells were associated with macrophages, with the majority localized near the cell membrane (FIG. 2B). Red (ALEXA FLUOR 550, Molecular Probes, Inc., Eugene, Oreg.) Phalloidin and GFP expressing bacteria were colocalized. 3D confocal z stacks show actin rings (red) surrounding bacterium (green and yellow) following 1.5-hour co-incubation (FIG. 2C). Fixed and silicified bacteria internalized for 24 hours were associated with LYSOTRACKER Red (Molecular Probes, Inc., Eugene, Oreg.) positive vesicles (FIG. 3B and FIG. 8B), confirming trafficking along the endosomal pathway into lysosomes.

Additional macrophages treated with 24-hour silicified bacteria for one hour were dehydrated, incubated with HMDS, and sputter-coated with 4-5 nm gold for SEM imaging. Scanning electron micrographs show bacteria (false-colored yellow) wrapped in macrophage filopodia at various magnifications (FIG. 2D) in agreement with the confocal microscopy imaging results. The morphology of the silicified bacteria appears structurally intact and not changed after rigorous processing steps.

Intracellular Trafficking of Silicified Bacterium

Figure 3:
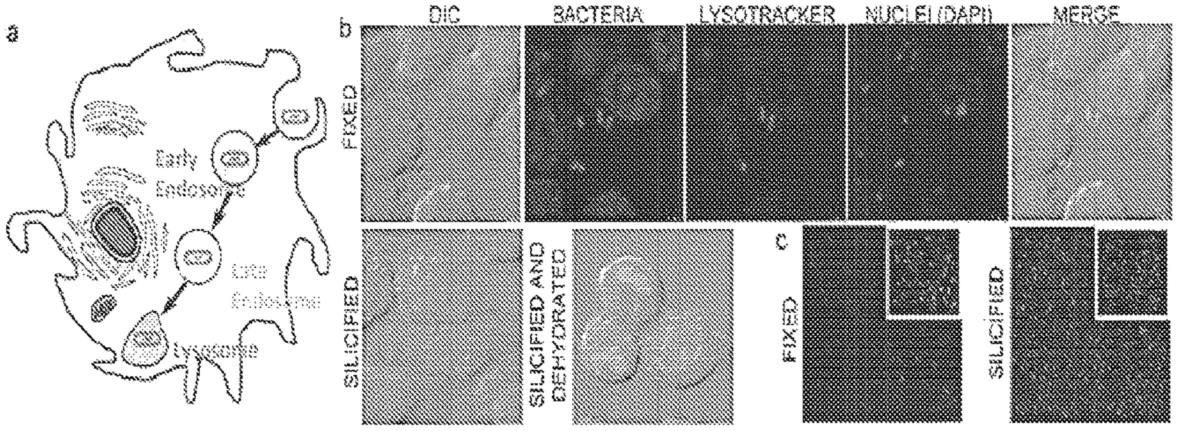
FIG. 3. Intracellular trafficking of silicified GFP-*Salmonella typhimurium* LT2. (A) Schematic showing phagocytosis and intracellular trafficking of bacteria and maturation of the host phagosome (early endosome) to late endosomes and then acidic lysosomes. (B) Confocal DIC illumination and fluorescent images (independent and merged) of fixed bacteria and LYSOTRACKER Red DND-99 (Molecular Probes, Inc., Eugene, Oreg.) labeled lysosomes in RAW macrophages. The bottom row contains merged images of silicified or silicified, dehydrated and rehydrated bacteria following internalization by RAW macrophages. (C) Fluorescent images of GFP bacteria (cell-independent; green) treated with LYSOTRACKER Red DND-99 (Molecular Probes, Inc., Eugene, Oreg.) for 24 hours at 37° C. The red channel (excitation 594, lysosomes) is shown as large images with inserts showing the green (excitation 488 nm, bacteria) channel.

A schematic showing cellular uptake of silicified bacteria into endosomes, with maturation of bacteria-laden vesicles into acidic lysosomes is shown in FIG. 3A. The intracellular fate of bacterium in macrophages was explored using fluorescent microscopy. Following cellular uptake, internalized bacterium colocalized with LYSOTRACKER Red (Molecular Probes, Inc., Eugene, Oreg.) lysosomes (FIG. 3B). This was true for control and dehydrated/rehydrated silicified bacteria. However, nonspecific association of LYSOTRACKER (Molecular Probes, Inc., Eugene, Oreg.) increased following silicification (FIG. 3C) due to enhanced absorptive properties, making the use of LYSOTRACKER (Molecular Probes, Inc., Eugene, Oreg.) to support localization of bacteria in lysosomes less reliable.

Activation of APC by Silicified Gram-Negative Bacteria

Figure 4:
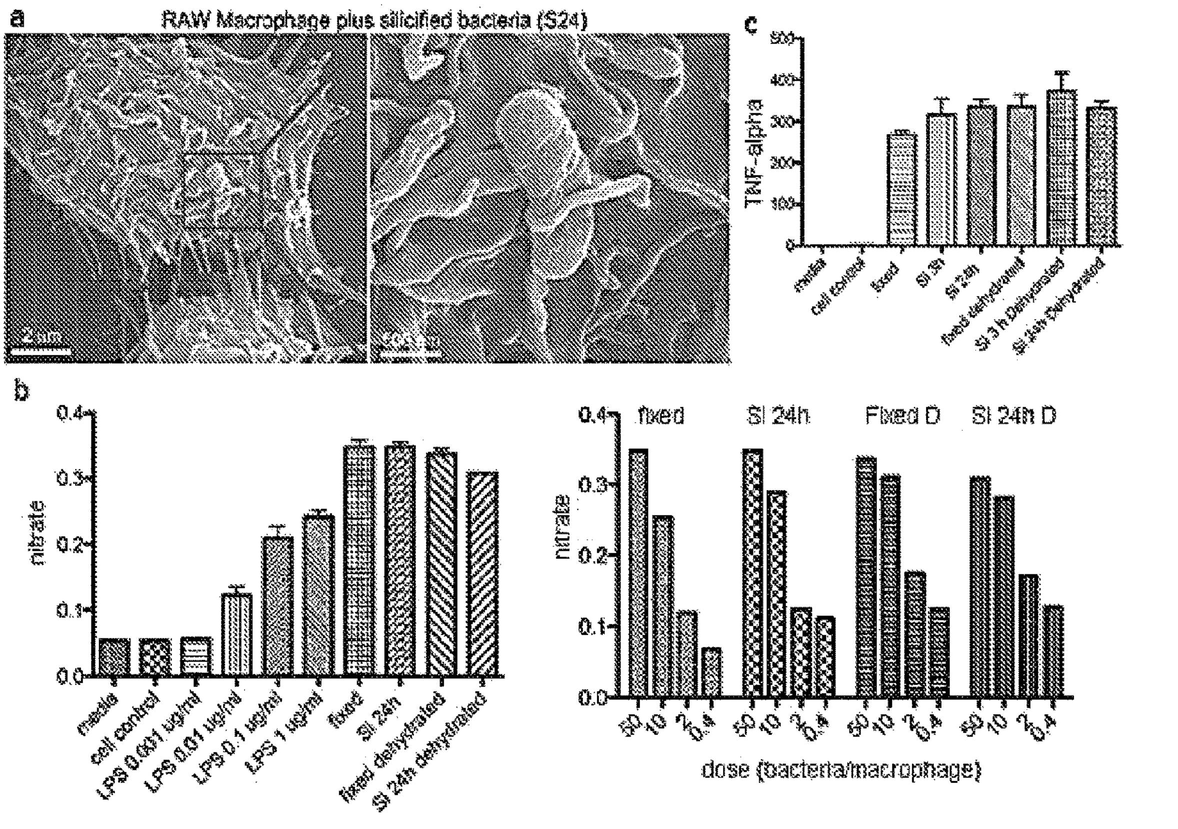
FIG. 4. Stimulation of cytokine and ROS production in RAW 264.7 murine macrophages by silicified *Salmonella typhimurium* LT2. (A) SEM images showing the capture of a bacterium (false-colored red) by a RAW macrophage. (B) Greiss assay showing production of nitrate ion 24 hours after introduction of LPS (titrated) or bacteria to RAW macrophages (50:1; left). To the right is nitrate production in response to titrated doses of treated bacteria. (C) ELISA-derived measurements of TNF-α production 24 hours after introduction of bacteria to RAW macrophages.

The capture of a 24-hour-silicified Gram-negative bacterium (pseudo-colored pink) by a RAW macrophage is shown in two scanning electron micrographs at different magnifications (FIG. 4A). Filopodia (i.e., phagocytic tentacles) rising from the macrophage is seen surrounding the bacteria. Filopodia anchor the bacteria long enough for lamellipodium to protrude from the cell to engulf the bacterium.

The ability of siloxane bacteria replicas to activate macrophages was examined by monitoring reactive oxygen species and the pro-inflammatory cytokine TNF-α in the supernatant of RAW 264.7 cells following a 24-hour incubation with fixed (control), freshly silicified, or dehydrated/rehydrated *Salmonella typhimurium*. Elevations in TNF-α expression were seen for fixed, three-hour silicification bacteria, and 24-hour silicification bacteria, with and without dehydration (FIG. 4C). Using the Greiss assay to measure nitrate, LPS caused a dose dependent increase in nitrate production. Fixed and silicified bacteria, with and without exposure to dehydration, produced similar, high levels of nitrate production (FIG. 4B), supporting activation of reactive oxygen species and exposure of pathogen associated molecular patterns (PAMPs). Despite an increase in ROS following exposure to bacteria, the rate of proliferation of RAW cells exposed to bacteria (fixed or silicified) as similar to that of untreated control cells (FIG. 9B).

Activation of BMDC and Antigen Presentation

The ability of siloxane bacteria replicas to activate APC and to deliver the model antigen ovalbumin was evaluated next. BMDC were incubated with biomineralized ovalbumin-transformed DH5-α bacteria for three days, and then evaluated for phenotype, stimulatory capacity, and antigen presentation. A schematic showing uptake, antigen processing, and peptide presentation on the cell surface in association with major histocompatibility complex (MHC) I is presented in FIG. 5A. Following culture in GM-CSF and a 72-hour incubation with silicified bacteria, BMDC were entirely positive for CD11c (FIG. 5B), an integrin glycoprotein expressed by myeloid monocyte, macrophage and dendritic cells. Both control untreated and LPS-treated BMDC were negative for surface expression of the ovalbumin peptide (SIINFEKL, SEQ ID NO:1)-MHC I complex. Exposure to fixed or siloxane ovalbumin-transformed DH5-α resulted in greater than 10% of BMDC being positive for the complex, supporting both processing and presentation of antigen presented by bacteria. LPS stimulated expression of the co-stimulatory molecule CD86, with bacteria expressing even higher levels.

Figure 5:
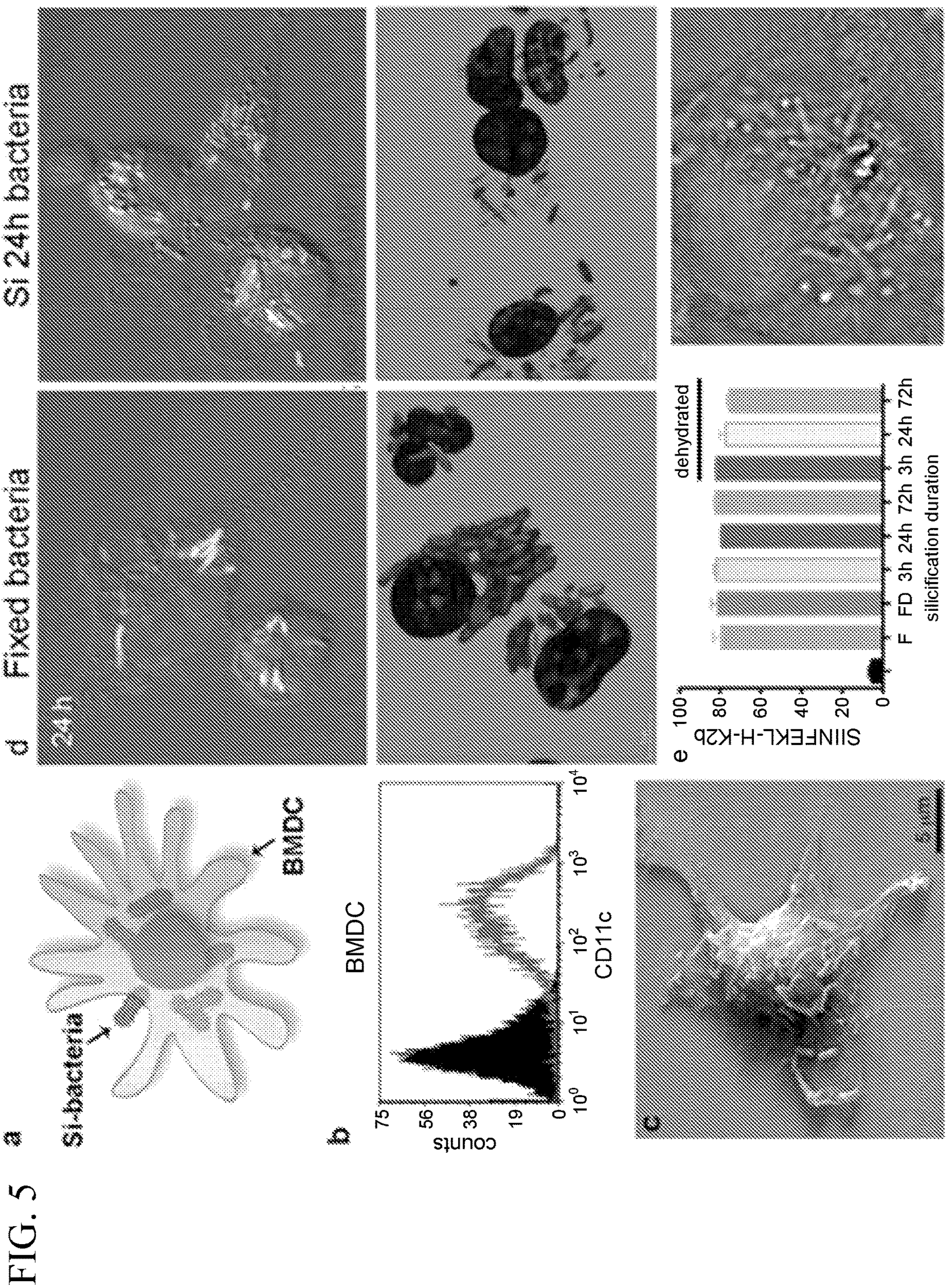
FIG. 5. Processing and presentation of antigen (ovalbumin) following internalization of biomineralized Gram-negative bacteria by bone marrow-derived dendritic cells (BMDC). (A) Schematic diagram showing internalization of silicified bacteria by BMDC. (B) Flow cytometry analysis of CD11c expression by BMDC. (C) Scanning electron micrograph showing association of false-colored (blue) bacteria and BMDC. (D) Merged DIC illumination and confocal fluorescent images showing BMDC 24 hours after adding fixed or 24-hour silicified (Si 24 h, higher magnification image shown in the bottom right) bacteria. 3D confocal images of BMDC stained with anti-LPS FITC (green) and anti-LAMP-1 PE (red) antibodies [nucleic (DAPI) shown in blue]. (E) Presentation of H-2K$^b$-SIINFEKL (SEQ ID NO:1) on BMDC 72 hours after introduction of silicified ovalbumin (OVA) transformed DH5-α bacteria cells.

The relative size of the bacteria in comparison to BMDC is seen in scanning electron of BMDC one hour after addition of siloxane bacteria (FIG. 5C). Bacteria have been false-colored blue to emphasize their location. In FIG. 5D, merged confocal DIC illumination and fluorescent images show BMDC 24 hours after adding fixed or 24-hour silicified (Si 24 h) bacteria. Green is anti-LPS FITC antibody, red is anti-LAMP-1 PE and blue is DAPI. In contrast to the abundant colocalization of LAMP-1 and LPS labeled bacteria, silicified bacteria are weakly labeled by both antibodies, suggesting that detergent-mediated permeability of the BMDC membrane prior to labeling was only partially successful in silicified cells. A single silicified cell is magnified in the lower right image. Processing of ovalbumin by BMDC (i.e. SIINFEKL (SEQ ID NO:1) presentation by $H\text{-}2K^b$) was equivalent in all cells following 72-hour exposure to fixed or silicified bacteria (FIG. 5E), regardless of the duration of the silicification process, supporting processing of silicified proteins.

Creating Pathogen Mimics Through Silicification of Cancer Cells

Figure 10:
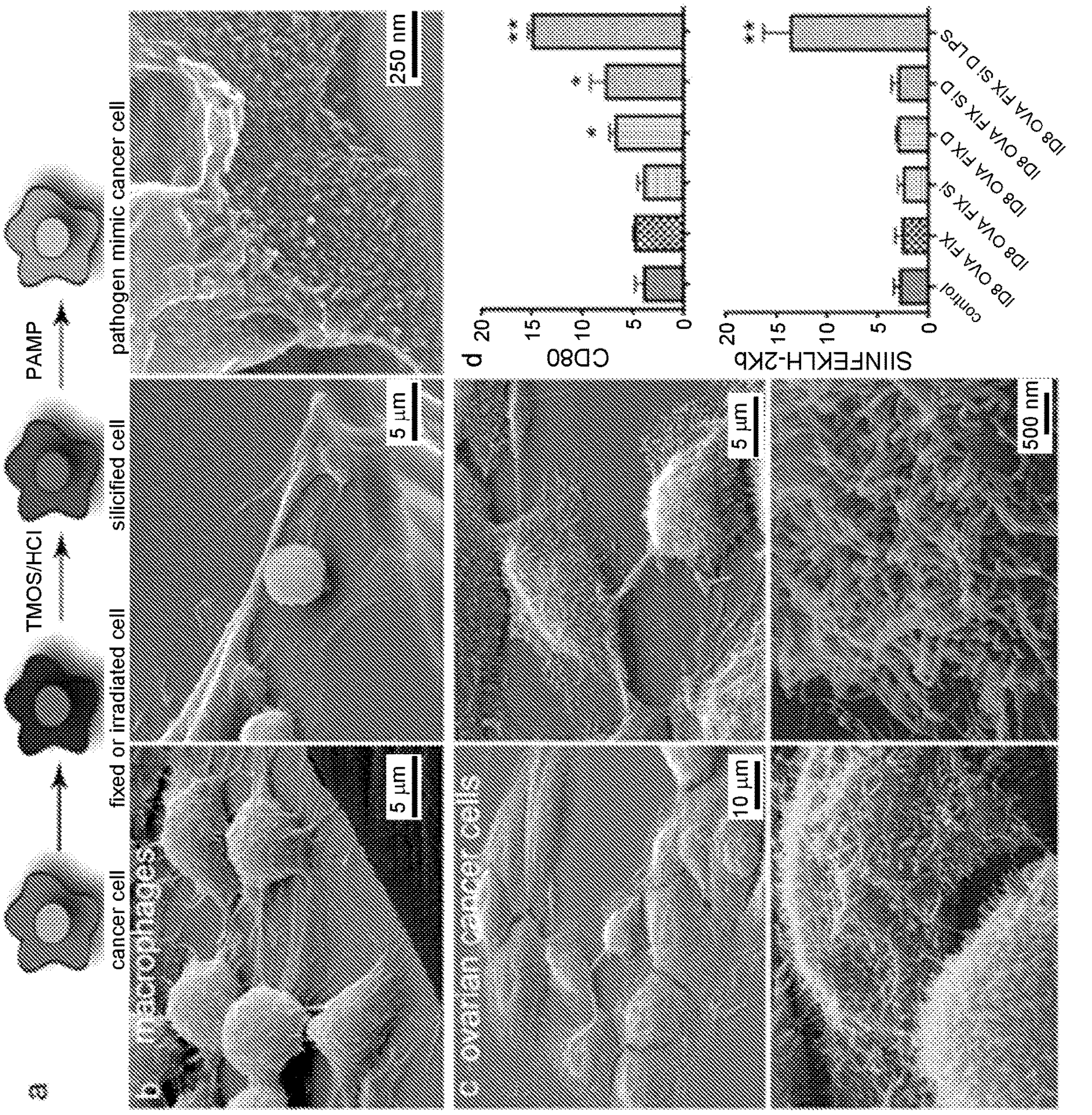
FIG. 10. Creating pathogen mimetic cancer cells through silicification. (A) Schematic showing the steps used to create pathogen-associated molecular patterns (PAMPs)-coated cancer cells. (B) SEM images of silicified and dehydrated RAW macrophages. A RAW cell has been sectioned (right panel) to expose the preserved intracellular structure of the silicified cell. (C) SEM images of silicified and dehydrated ID8-OVA ovarian cancer cells (C). ID8 cells are false-colored (bottom panels) to emphasis preservation of surface morphology. (D) BMDC were incubated with silicified cancer for 72 hours. Activation of BMDC by fixed (4% paraformaldehyde 10 minutes), silicified (Si), dehydrated ID8-OVA cells is shown graphically using CD80 (flow cytometry) as a metric. Antigen presentation (SIINFEKL (SEQ ID NO:1)-H-2Kb) by treated BMDC is shown in the bottom graph (*$p<0.05$; **$p<0.001$ compared to no treatment control cells).

The schematic in FIG. 10A shows steps involved in transforming cancer cells into pathogen mimics. Following fixation or irradiation, cancer cells are silicified under mild acidic conditions in TMOS solution, followed by surface adsorption of bacteria-derived PAMPs onto the silicified cells. The SEM images in FIG. 10B and FIG. 10C show preservation of cellular structure by silicification, exemplified by maintenance of thin, non-adherent homotypic intercellular connections (i.e., tunneling nanotubes) between RAW macrophages (FIG. 10B) and cancer cells (FIG. 10C). Retention of intracellular features is revealed in the severed cell shown at two magnifications in the two right SEM images in FIG. 10B, while FIG. 10C shows low and high magnification images of ID8-OVA ovarian cancer cells, with retention of nanoscale cellular projections highlighted through false coloring in the bottom two images.

Activation and presentation of a model antigenic peptide (i.e., SIINFEKL, SEQ ID NO:1) in association with H-2Kd by C57BL/6 BMDC 72 hours following introduction of control or modified ID8-OVA cells was probed using fluorescent antibody labeling and flow cytometry (FIG. 10D). Using CD80 as a metric for cell activation, the results show that fixed or silicified ID8 OVA cells failed to stimulate BMDC, however, dehydrated silicified ID8-OVA cells stimulated a significant increase in CD80 expression that was doubled by surface adsorption of the silicified ID8-OVA cells with LPS (FIG. 10D). Only LPS silicified ID8-OVA cells significantly stimulated antigen processing and presentation by BMDC, demonstrating that immune stimulation (with PAMPs) is involved in both activation of BMDC and antigen presentation.

Figure 11:
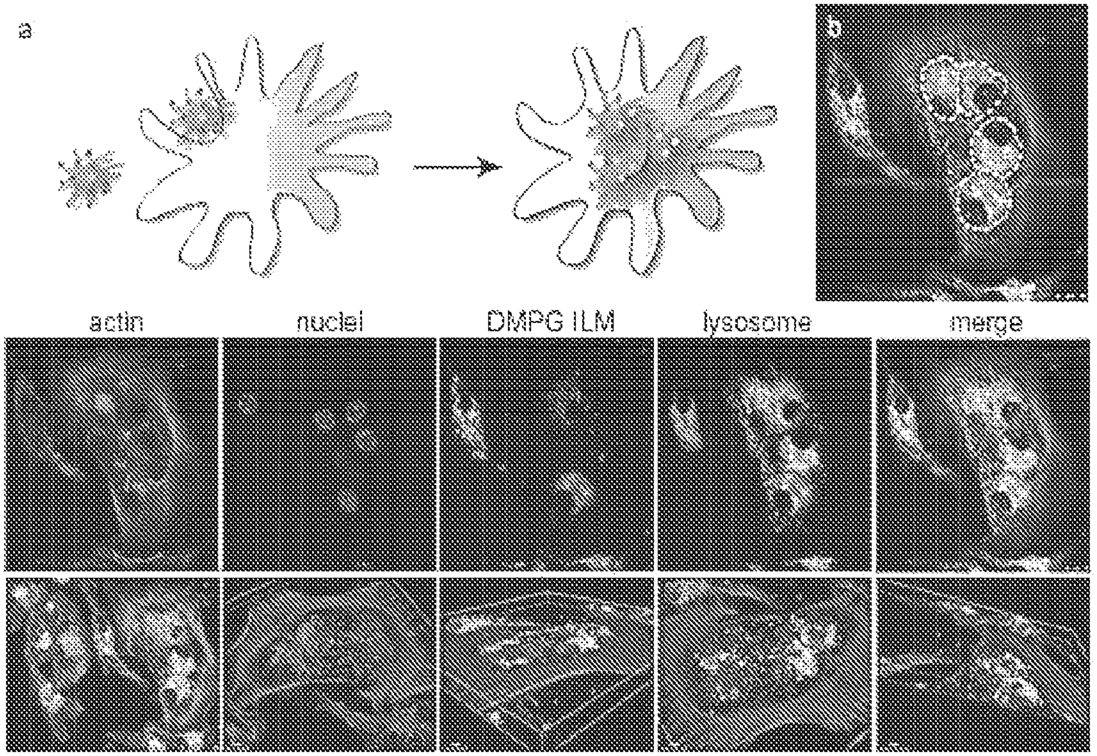
FIG. 11. Dendritic cell (DC) phagocytosis of pathogen mimetic cells. (A) Schematic showing DC internalization of cells coated with TLR4 ligand presenting nanoparticles (DMPG ILM). (B) 2D (single fluorophore and merged) and 3D (blend and surface-rendered) confocal micrographs showing a DC with four internalized ILM nanoparticle-treated DC (two hours after addition of ILM nanoparticles (DYLIGHT 488; green, Thermo fisher Scientific, Inc., Waltham, Mass.) to DC cell culture). Cells were stained with anti-LAMP-1 antibody (lysosome, cyan), phalloidin (actin, red) and DAPI (nuclei, blue).

BMDC that were incubated with a high dose of immunogenic lipid coated mesoporous (ILM) nanoparticles, presenting the TLR4 ligand MPL, stimulated internalization of BMDC by like cells (schematic shown in FIG. 11A). This experiment was carried out by incubating BMDC with green (AF488) fluorescent ILM nanoparticles for two hours, followed by fixation and staining with rhodamine phalloidin (red; nuclei shown in blue) and anti-LAMP-1 AF647 (cyan; FIG. 11B). Shown in the top right image is a confocal micrograph of a BMDC with four internalized BMDC circled with dotted white lines. Single fluorophore and merged imaged from a single z plane are shown in the middle row. A projection image created from a series of z planes is shown in the bottom row left image, while 3D blend and surface rendered images from the z-stack are shown at various angles. This work demonstrates that masking of cells with pathogenic molecules stimulates internalization by BMDC.

Figure 12:
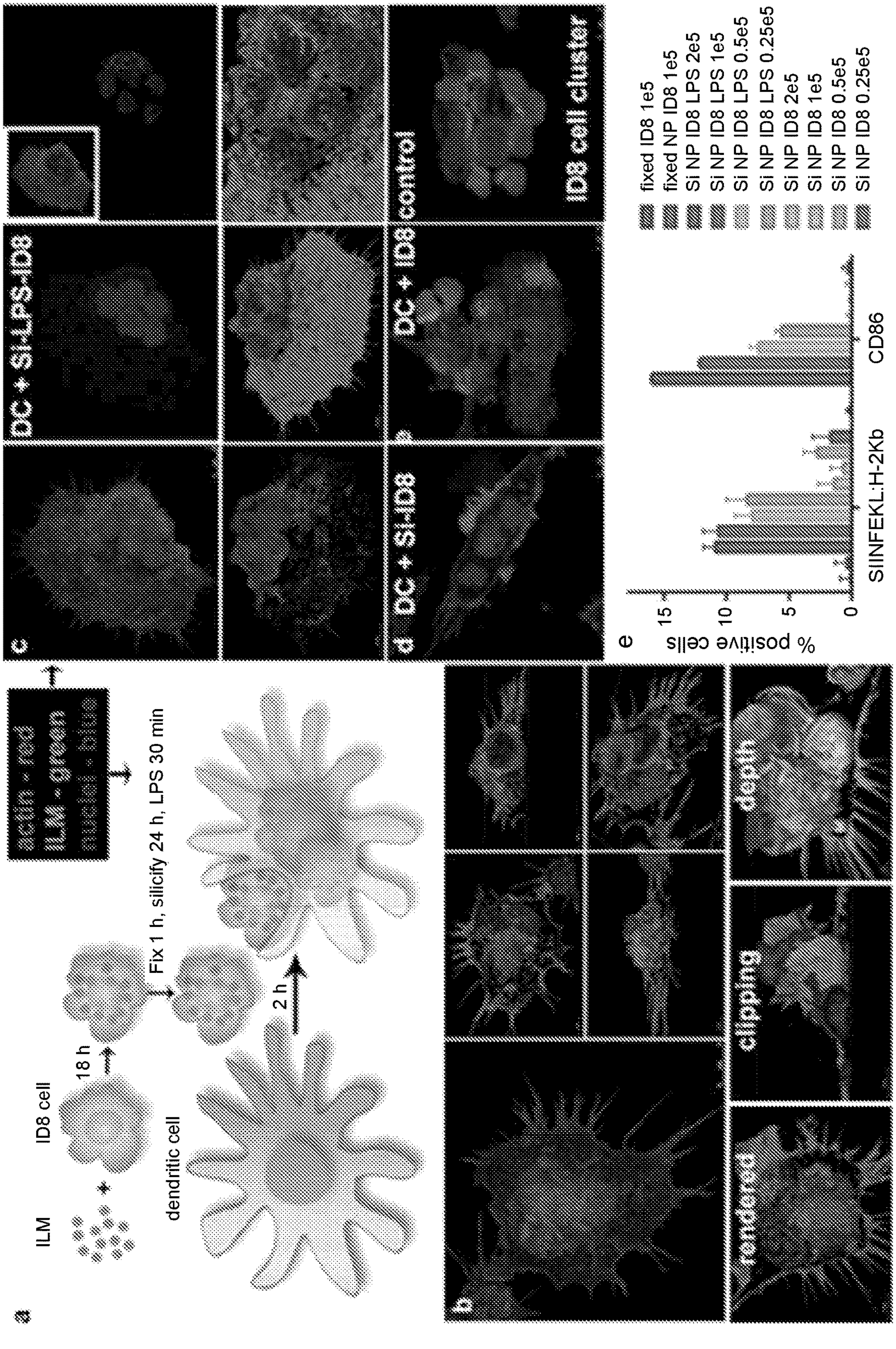
FIG. 12. Cancer cell silicification and PAMP adsorption stimulates BMDC internalization of cancer cells. (A) Schematic diagram illustrating ID8-OVA-GFP internalization of DYLIGHT 488 (Thermo fisher Scientific, Inc., Waltham, Mass.) immunogenic (ILM) nanoparticles, followed by fixation, silicification, and LPS adsorption, and then uptake by BMDC. (B) Confocal 2D images of two distinct BMDC following a two-hour incubation with Si-ID8-OVA-GFP cells. (C) Confocal 3D images of two distinct BMDC following a two-hour incubation with Si-ID8-OVA-GFP cells. (D) Confocal images of BMDC following a two-hour incubation with Si-ID8 cells or fixed ID8 cells. Red: actin; blue: nuclei, green: ILM or GFP ID8 cells. (E) Flow cytometry data showing dose-dependent DC activation (CD86) and antigen presentation (SIINFEKL(SEQ ID NO:1)-H-2Kb) by BMDC in response to treatment with titrated silicified LPS-ID8-OVA or control cancer cells.

As illustrated in the schematic in FIG. 12A, IL8-GFP-OVA ovarian cancer cells were treated with green ILM nanoparticles for 18 hours, followed by fixation, silicification and surface coating with LPS. These pathogen-disguised cancer cells (LPS-ID8-GFP-OVA) were added to cultured BMDC for two hours and then their uptake was visualized using confocal microscopy (FIG. 12B-D; phalloidin-red; nuclei-blue, cancer cells-green). Two unique BMDC, each with 4-5 internalized cancer cells are shown in 2D projection and 3D confocal images in FIG. 12B and FIG. 12C. All images in FIG. 12B except for the top left were surface rendered, with images in the bottom shown with clipping to see inside the BMDC and colored using a depth scale to emphasis the clustering of internalized cancer cells around the BMDC nucleus. Single and merged fluorophore projection images are shown in the top row of FIG. 12C, with internalized cancer cells clustered in the perinuclear region of the BMDC. FIG. 12D (left) shows a BMDC after culture with silicified ID8 cells without LPS. While several BMDC were located that had internalized silicified cancer cells, the occurrence was rare. BMDC incubated with fixed only ID8 cells failed to internalize cancer cells, however, transfer of fluorescent nanoparticles from the cancer cells to the BMDC occurred (FIG. 12D, middle). The fixed only cancer cells were predominantly found in BMDC-free clusters (FIG. 12D, right). This work indicates that silicification alone does not favor internalization of cancer cells by BMDC, but that uptake involves masking the cancer cells with pathogen-derived molecules.

Figure 13:
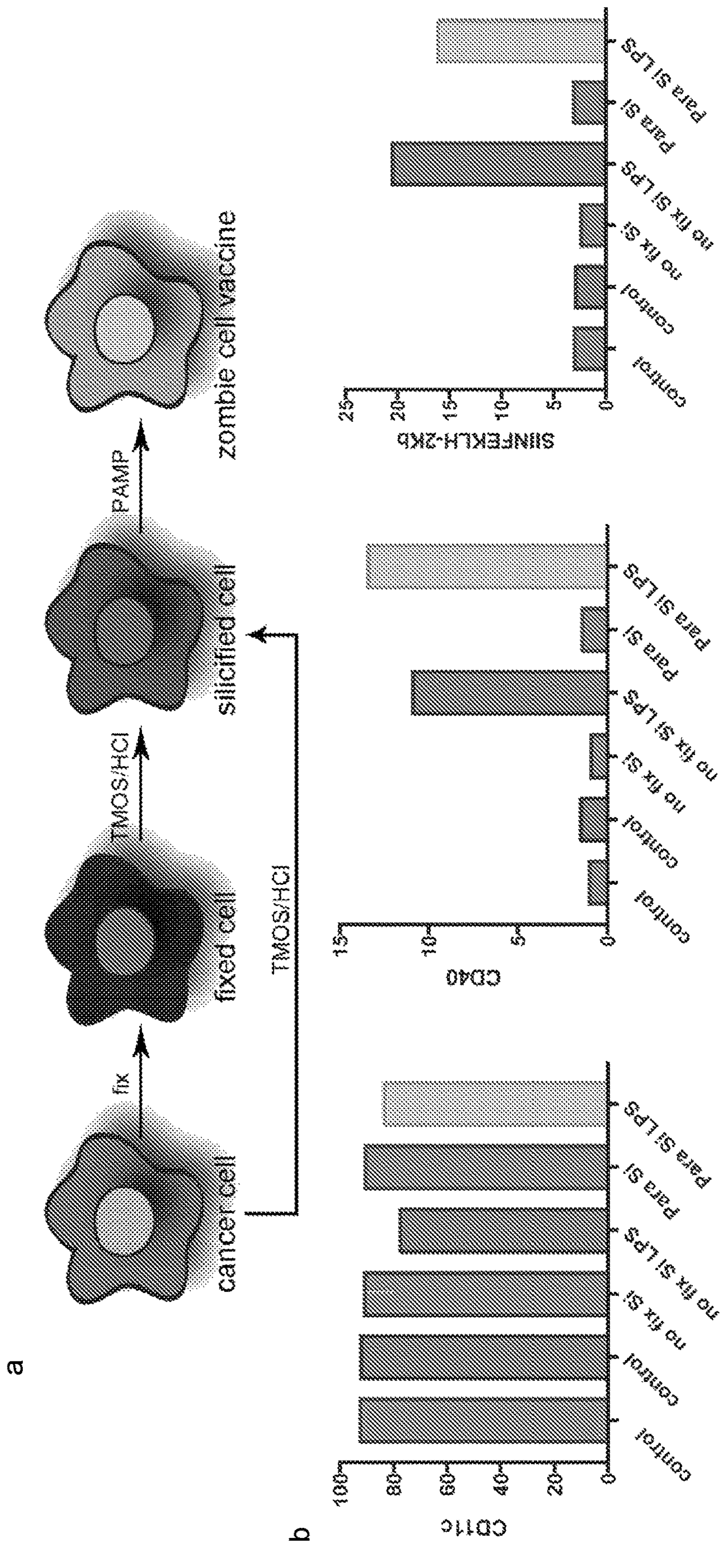
FIG. 13. Silicification without fixation. (A) Schematic diagram of primary and secondary silane modification leading to optimal binding of PAMPs to the cell surface. (B) Flow cytometry analysis of CD11c, CD40, and SIINFEKL (SEQ ID NO:1)-H-2Kb expression by BMDC following 72-hour incubation with silicified (Si) ID8-OVA cells (with and without prior fixation in 4% paraformaldehyde for 10 minutes).

Fixed and silicified ID8-OVA cells failed to activate BMDC using CD86 as a metric for activation (FIG. 12E). On the contrary, silicified, LPS-ID8-OVA cells activated BMDC and further stimulated antigen (SIINFEKL(SEQ ID NO:1)-H-2K$^b$) presentation in a dose dependent manner. While there was some presentation of antigen in BMDC treated with silicified ID8 cells in the absence of LPS, presentation was variable, supporting the idea that the presence of LPS (PAMPs) facilitates BMDC internalization of cancer cells and processing of antigens. LPS reduces expression of CD11c on dendritic cells. Silicification of ID8-OVA cells without prior fixation and LPS adsorption resulted in similar reductions in CD11c expression by BMDC (FIG. 13, left), supporting that fixation is not essential for cell silicification and LPS binding. CD40 expression was slightly reduced (FIG. 13, middle) and antigen presentation was slightly increased (FIG. 13 right) when the cancer cells were silicified in the absence of fixation, supporting better processing of antigens in the absence of paraformaldehyde fixation.

Figure 14:
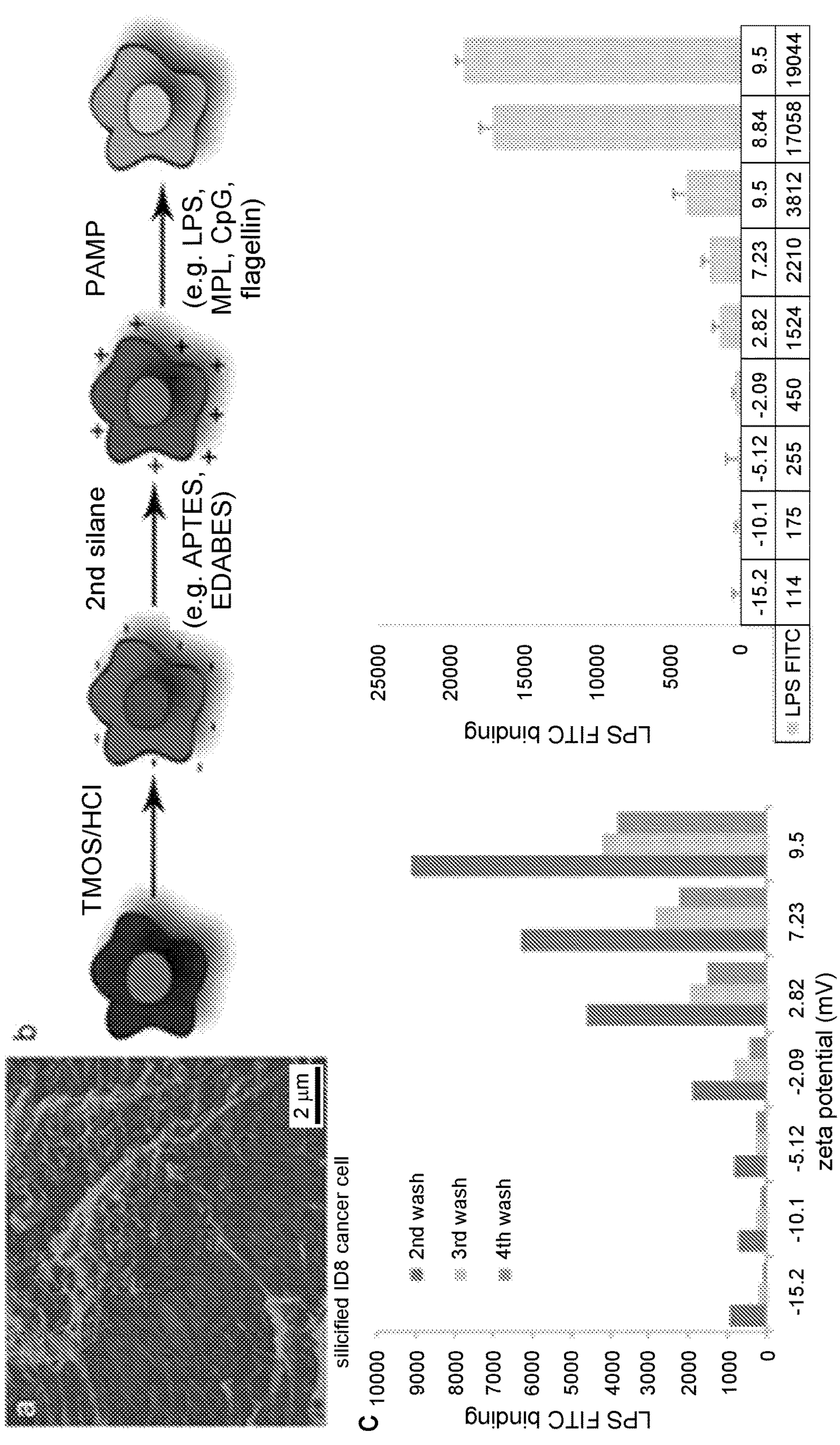
FIG. 14. Engineering the surface of silicified cells to maximize PAMP adsorption. (A) False-colored SEM of silicified ID8 ovarian cancer cells. (B) Schematic diagram showing the steps involved in optimizing the cell surface for optimal binding by PAMPs. (C) Silicified ID8 cancer cells were dehydrated with acetone and modified under variable conditions with aminosilane (APTES or EDABES) to generate biomineralized cells with variable surface potentials (charges). Graphs show the relationship between Zeta potential and surface adsorption by LPS FITC (right) and retention of the LPS-FITC following sequential washes (left).

Optimizing PAMP binding to the surface of silicified cancer cells included secondary silane modification following primary silicification in TMOS. A schematic of the processing steps is shown in FIG. 14B. TMOS-silicified cancer cells were treated with either the monoamine APTES or the diamine EDABES. Changes in zeta potential were monitored to track amino silylation following sequential wash steps. Minimal change in surface potential following the 3$^{rd}$ wash supported stable amine modification of the silicified cancer cells (FIG. 14C, left). Binding by LPS-FITC was estimated using a microtiter plate reader at 488/525 nm ex/em. Cationic surface potential was positively correlated with LPS-FITC adsorption on the cancer cell (FIG. 14C, right).

Figure 15:
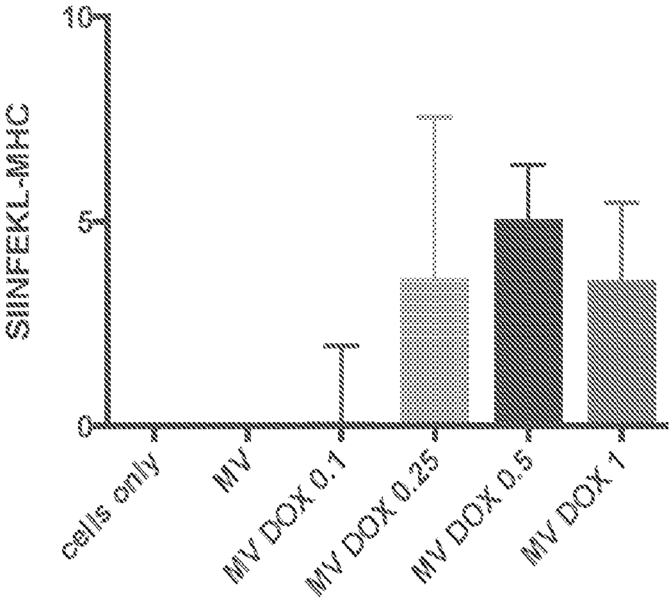
FIG. 15. Immunogenic cancer cell-derived microvesicles deliver antigen to BMDC. ID8-OVA cancer cells were treated with variable doses (0.1-1 μg/ml) of the immunogenic cell death (ICD)-inducing anthracycline, doxorubicin (DOX) for 24 hours, followed by isolation of microvesicles, which were then added to BMDC for 72 hours. Shown graphically is flow cytometry analysis of antigen (SIINFEKL(SEQ ID NO:1)-H-$2K^b$) presentation by the treated BMDC.

The ability to create immunogenic cancer cell-derived silicified microvesicles (MV) was demonstrated by treating ID8-OVA cancer cells with doxorubicin (DOX) and 24 hours later isolating microvesicles in the cell supernatant and silicifying them for 24 hours. The siloxane microvesicles were incubated with BMDC at increasing doses and presentation of SIINFEKL(SEQ ID NO:1)-H-2K$^b$ (MHC) was measured by flow cytometry after 72 hours (FIG. 15). While siloxane microvesicles from control ID8-OVA cells (MV) did not stimulate antigen (OVA) processing, siloxane microvesicles derived from cells pretreated with the immunogenic cell death inducing anthracycline doxorubicin stimulated antigen processing. This data supports that cancer cells or cancer cell-derived fragments need to present immunogenic molecules to activate BMDC to process and present antigens.

This disclosure describes rapid internalization and enduring activation of antigen presenting murine RAW 264.7 macrophage-like cells or bone-marrow-derived dendritic cells (BMDC) by fixed, silicified Gram-negative bacteria, supporting the ability of bacterial PAMPs to engage receptors on the surface of antigen presenting cells (APC). Supplemental LPS added to the culture media failed to enhance immune responses to siloxane bacteria, further supporting that LPS on the surface of bacteria is accessible to TLR receptors on the surface of APC. RAW macrophages stimulated with *E. coli*-derived LPS produce nitric oxide and TNF-α. In this disclosure, silicified Gram-negative *S. enterica* serovar *Typhimurium* LT2 stimulated secretion of both TNF-α and reactive oxygen species by RAW cells. Silicification and dehydration of genetically engineered *Escherichia coli* expressing the model antigen ovalbumin did not deter processing and presentation of antigen by BMDC, as demonstrated through detection of the SIINFEKL (SEQ ID NO:1) peptide in association with the major histocompatibility molecule (MHC) H-2K$^b$.

This disclosure further demonstrates, using murine cells and scanning electron microscopy, that silicification successfully preserves delicate cellular features, both within, on the surface of, and between cells. Nanoscale surface features and thin, intercellular homotypic connections between macrophages or ovarian cancer cells were preserved throughout the drying process and in the presence of the high vacuum and voltage transitions present in the EM.

Figure 7:
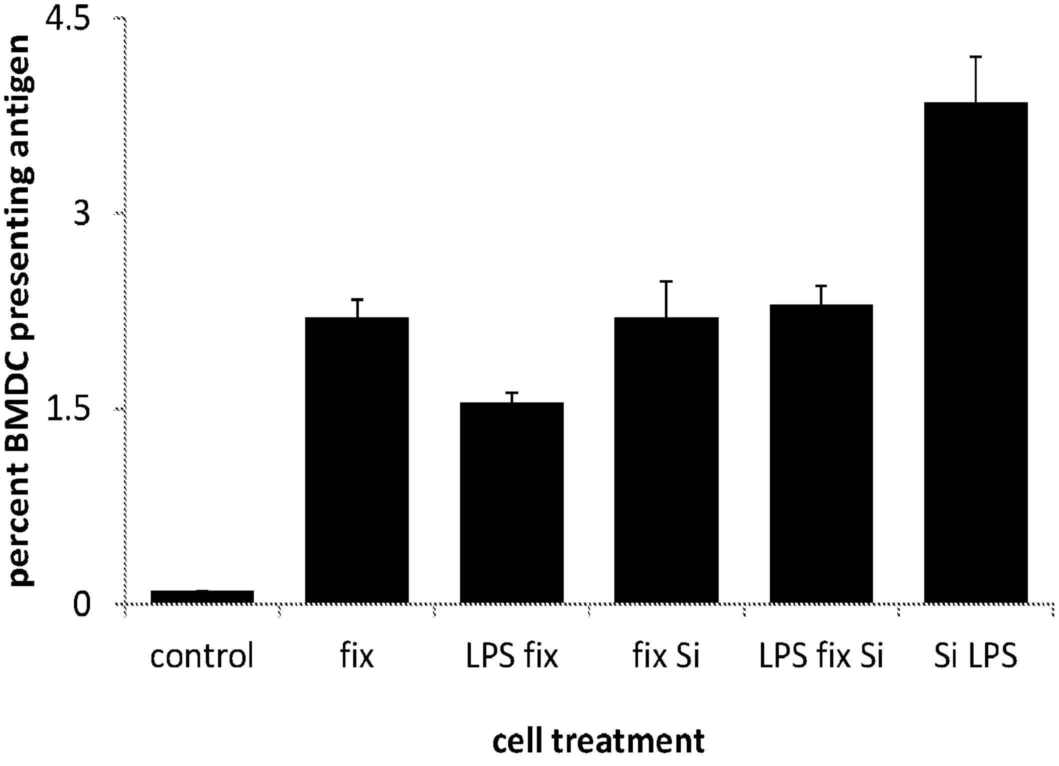
FIG. 7. Dendritic cell processing and presentation of a model antigen delivered by silicified (siloxane) cancer cells. Ovalbumin transformed ID8 ovarian cancer cells were incubated with a solution of LPS in PBS before (LPS fix, LPS fix Si) or after (Si LPS) fixation and silicification, and then siloxane cancer cells were added to C57BL/6 murine bone marrow-derived dendritic cells at a ratio of one cancer cell to each dendritic cell. After 3 days in culture, dendritic cells were analyzed using flow cytometry for the presence of ovalbumin peptide (SIINFEKL, SEQ ID NO:1) presented on the cell surface in association with MHC class I. The percent of dendritic cells positive for antigen presentation following treatment with siloxane cancer cells is presented in the graph.

Abundant presentation of PAMPs on the surface of silicified cancer cells stimulated internalization by and activation of BMDC. Cell silicification therefore both preserves cells and can functionalize the cell surface. This disclosure therefore discloses creating cell replicas that mimic pathogens, thereby stimulating DC internalization, activation, and antigen processing. While cancer cell silicification alone is not necessarily sufficient to stimulate DC uptake and activation, PAMP-functionalized pathogen mimics stimulated a dose-dependent increase in both surface expression of costimulatory molecules and antigen presentation. The ability to further functionalize the silica surface on biomineralized cells (e.g., amino, carboxy, or covalent attachment) enables tailoring the cell surface for high affinity binding to a diverse array of immunogenic molecules. For example, the presence of LPS on silicified ovalbumin-transformed ID8 cancer cells stimulated an increase in processing and presentation of the SIINFEKL (SEQ ID NO:1) peptide on surface of bone marrow-derived dendritic cells in association with the MHC class I H-2 Kb allele (FIGS. 7 and 12E). The surface of a silicified cell may be functionalized to present one or more DAMPs in place of, or in addition to, any functionalization to present one or more PAMPs.

Lastly, this disclosure describes silicification of cancer cells without prior fixation, resulting in similar levels of DC activation and increased antigen presentation compared to paraformaldehyde-fixed, silicified cancer cells. The elimination of fixative is advantageous for clinical use, enabling the use of the silicified cancer cell pathogen mimics as personalized therapeutic cancer vaccines. While described herein in the context of an exemplary embodiment in which the silicified cancer cell is functionalized with LPS, the silicified cells, and methods of using silicified cells, can involve silicified cells functionalized with other moieties, as desired. For example, substituting the LPS subunit, MPL-A, for LPS can reduce (or even eliminate) the likelihood, extent, or severity of bacterial sepsis while preserving BMDC targeting and activation.

In summary, silicified cell replicas retain structural features, are immunogenic and stable, and deliver antigens to APC for effective processing and presentation. Absorption of pathogen-associated danger signals to the surface of silicified cancer cells increased the ability of APC to process antigen presented by the cancer cells. The entire cell need not be silicified and presented to generate the immunological effects. Subcellular fragments—e.g., exosomes, microvesicles, or apoptotic bodies—may be isolated and silicified. For example, a pathogen or cancer cell may be lysed, otherwise disrupted, or activated to stimulate secretion of vesicles with agents such as chemotherapeutics, liberating subcellular fragments. The subcellular fragments may be isolated and subjected to the silicification process described in detail herein to produce stabilized, immunogenic subcellular fragments. For example, microvesicles (e.g., shedding vesicles, ectosomes, oncosomes, shedding bodies, and/or microparticles) can be released from, for example, intact cancer cells. Their release from the cancer cell can be stimulated by cytokines (TNF-α, IFN-γ, IL-4) and/or LPS. The microvesicles can be biologically active and can create microniches that favor cancer metastases. Silicified cancer-cell-derived biovesicles, can therefore induce an immunological response against cancer cells. In some cases, the microvesicles can be functionalized with one or more PAMPs and/or one or more DAMPs, as described above in the context of silicified cells.

The ability of engineered, stable bacteria, pathogenic human cells, or fragments of such cells to harness and guide immune responses helps to address the global need for versatile effective vaccines.

Thus, this disclosure describes a pharmaceutical composition (e.g., a vaccine) that includes a silicified cell replica and method of preparing silicified cell replicas. The ability to silicify, for example, cancer cells and modify the surface with pathogen-derived immunogenic molecules results in enhanced activation and internalization by dendritic cells. These silicified cancer cell mimics have the potential to function as potent cancer vaccines, driving immune responses against patient-specific tumor neoantigens.

As used herein, “silicified cell replica” refers collectively to a silicified cell or a silicified cell fragment or silicified cell-derived body, such as, for example, a silicified exosome, a silicified microvesicle, or a silicified apoptotic body. The composition may be formulated with a pharmaceutically acceptable carrier. As used herein, “carrier” includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, “pharmaceutically acceptable” refers to a material that is not biologically or otherwise undesirable, i.e., the material may be administered to an individual along with a silicified cell replica without causing any undesirable biological effects or interacting in a deleterious manner with any of the other components of the pharmaceutical composition in which it is contained.

A silicified cell replica may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical can be administered via a sustained or delayed release.

Thus, a silicified cell replica may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, solution and the like. The formulation may further include one or more additives including such as, for example, an adjuvant. Exemplary adjuvants include, for example, pathogen-associated molecular patterns (PAMPs), such as Toll-like receptor (TLR) ligands, damage-associated molecular patterns (DAMPs), cytokines, proteins, carbohydrates, lectins, Freund’s adjuvant, aluminum hydroxide, or aluminum phosphate.

A formulation may be conveniently presented in unit dosage form and may be prepared by methods well known in the art of pharmacy. Methods of preparing a composition with a pharmaceutically acceptable carrier include the step of bringing the silicified cell replica into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of silicified cell replica administered can vary depending on various factors including, but not limited to, the specific silicified cell being administered, the weight, physical condition, and/or age of the subject, and/or the route of administration. Thus, the absolute amount of silicified cell replica included in a given unit dosage form can vary widely, and depends upon factors such as the species, age, weight and physical condition of the subject, and/or the method of administration. Accordingly, it is not practical to set forth generally the amount that constitutes an amount of silicified cell replica effective for all possible applications. Those of ordinary skill in the art, however, can readily determine the appropriate amount with due consideration of such factors.

In some embodiments, the method can include administering sufficient silicified cell replicas to provide a dose of, for example, from about 50 silicified cells/kg to about $1\times10^{10}$ silicified cells/kg to the subject, although in some embodiments the methods may be performed by administering the silicified cell replicas in a dose outside this range. In some of these embodiments, the method includes administering sufficient silicified cell replicas to provide a dose of from about 100 silicified cells/kg to $1\times10^{9}$ silicified cells/kg to the subject, for example, a dose of from about 1000 silicified cells/kg to about 10,000 silicified cells/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2=(\text{wt kg}^{0.425}\times\text{height cm}^{0.725})\times0.007184$.

In some embodiments, silicified cell replicas may be administered, for example, from a single dose to multiple doses per week, although in some embodiments the method can be performed by administering silicified cell replicas at a frequency outside this range. In certain embodiments, silicified cell replicas may be administered from about once every six months to about three times per week.

In some embodiments, a silicified cell replica can be any cell that expresses an antigen against which an immune response may be mounted. The antigen may be present in the cell or the cell may be transformed to express specific disease-related antigens. The immune response may involve an innate immune response, an acquired immune response, a humoral immune response, and/or a cell-mediated immune response.

A silicified cell replica can include any suitable type of cell or a subcellular fragment of any type of cell such as, for example, a bacterial cell or a tumor cell. Exemplary bacterial cells include *Salmonella* spp. (e.g., *S. typhimurium* LT2), *Mycobacterium* spp. (e.g., *M. tuberculosis* or *M. avium*), *Streptococcus* spp., *Staphylococcus* spp., *Pseudomonas* spp. (e.g., *P. aeruginosa*), *Burkholderia* spp. (e.g., *B. cenocepacia*). Exemplary tumor cells include cells derived from patient tumors, blood, ascites, or established tumor cell lines.

In some embodiments, the surface of the silicified cell replica may be modified to enhance the immunogenicity of the silicified cell. The silica surface readily binds to certain surface modifiers such as, pathogen-associated molecular patterns (PAMP) or damage-associated molecular patterns (DAMP). Exemplary PAMPs include lipopolysaccharide (LPS), monophosphoryl lipid (MPL), Poly IC, double-stranded RNA, lipoteichoic acid, peptidoglycan, viruses, and unmethylated CpG. DAMPS are endogenous molecules created upon tissue injury, such as heat shock proteins, high mobility group box 1, proteins such as hyaluronan fragments, and non-protein targets such as ATP, uric acid, DNA and heparin sulfate.

This disclosure also described methods that involve administering one or more silicified cell replicas to a subject in an amount effective to induce an immune response. In one aspect, such a method involves obtaining a cell that expresses an antigen against which an immune response is desired, preparing a silicified cell replica by silicifying the cell or a subcellular fragment of the cell, and administering the silicified cell replica to a subject in an amount effective to induce the subject to produce an immune response directed against the antigen.

In some embodiments, the silicified cell replica can be administered to the subject in a pharmaceutical composition, described in detail above, that includes an effective amount of a pharmaceutically acceptable adjuvant.

The silicified cell replica can include any suitable silicified bacterial cell, any suitable silicified tumor cell, or any silicide subcellular fragment from any suitable bacterial cell or any suitable tumor cell described in more detail above.

In another aspect, this disclosure describes a method for treating a subject having, or at risk of having a bacterial or other opportunistic infection or developing cancer. Generally, the method includes obtaining a bacterial cell that the subject is, or is at risk, of being infected by, preparing a silicified cell replica by silicifying the bacterial cell or a subcellular fragment of the bacterial cell, and administering the silicified cell replica to the subject in an amount effective to ameliorate at least one symptom or clinical sign of infection by the bacterial cell.

In this context, "at risk" refers to a subject that may or may not actually possess the described risk. Thus, for example, a subject "at risk" of infection by a microbe is a subject present in an area where individuals have been identified as infected by the microbe and/or is likely to be exposed to the microbe even if the subject has not yet manifested any detectable indication of infection by the microbe and regardless of whether the subject may harbor a subclinical amount of the microbe.

As used herein, "treat" or variations thereof refer to reducing, limiting progression, ameliorating, or resolving, to any extent, the symptoms or signs related to a condition. Thus, a "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject.

In some embodiments, the bacterial cell may be obtained from the subject, thereby providing a personalized vaccine.

In another aspect, this disclosure describes a method for treating a subject having, or at risk of having, a tumor.

Generally, the method includes obtaining a tumor cell that the subject has or is at risk of having, preparing a silicified cell replica by silicifying the tumor cell or a subcellular fragment of the tumor cell, and administering the silicified cell replica to the subject in an amount effective to ameliorate at least one symptom or clinical sign of having the tumor.

In this context, a subject "at risk" for developing a specified condition (e.g., having a tumor) is a subject that possesses one or more indicia of increased risk of having, or developing, the specified condition compared to individuals who lack the one or more indicia, regardless of the whether the subject manifests any symptom or clinical sign of having or developing the condition. As used herein, "symptom" refers to any subjective evidence of disease or of a patient's condition; "sign" or "clinical sign" refers to an objective physical finding relating to a particular condition capable of being found by one other than the patient.

Thus, once again, the treatment may be prophylactic or therapeutic.

In some embodiments, the tumor cell can be obtained from the subject, thereby providing personalized treatment.

In one exemplary application, silicified tumor cells may be used to create personalized tumor vaccines in which cancer cells and their constituents are fixed in their native conformations, surface-modified with pathogen-associated molecular patterns (PAMPs), dehydrated, and ready for use indefinitely. For example, tumor cells may be silicified to stimulate diverse cancer-specific immune responses to multiple tumor antigens.

In the preceding description and following claims, the term "and/or" means one or all of the listed elements or a combination of any two or more of the listed elements; the terms "comprises," "comprising," and variations thereof are to be construed as open ended i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Materials

| Cell lines/bacteria | Source | Accession No/ Catalogue # |
|---|---|---|
| RAW 264.7 | ATCC (Manassas, VA). | TIB-71 |
| *E. coli* DH5-α-ovalbumin | Addgene (Cambridge, MA) | 64599 |

-continued

| | | |
|---|---|---|
| *Salmonella enterica* serovar Typhimurium LT2 | Dr. Stanley Maloy, San Diego State University, San Diego | |
| ID8-OVA-mVEGF-GFP and ID8-OVA ovarian cancer cells | Gift from Dr. George Coukos, University of Pennsylvania, PA, USA | |

| | Source | Catalogue # |
|---|---|---|
| Antibodies | | |
| rabbit anti-α-tubulin antibody-ALEXA FLUOR 647 | Abcam (Cambridge, MA) | EP1332Y |
| Mouse anti-α-tubulin antibody-ALEXA FLUOR 488 | ThermoFisher Scientific, Inc. (Grand Island, NY) | clone B-5-1-2 |
| Cytokines | | |
| Murine GM-CSF | PeproTech, Inc. (Rocky Hill, NJ) | 315-03 |
| Chemicals | | |
| Lipopolysaccharide (LPS), LPS-FITC (2-10 μg FITC/ mg LPS) | Sigma-Aldrich (St. Louis, MO) | L3024, F3665 |
| DYLIGHT fluorophores | ThermoFisher Scientific, Inc. (Grand Island, NY) | 46403, 46413 |
| LYSOTRACKER Red DND-99 | ThermoFisher Scientific, Inc. (Grand Island, NY) | L7528 |
| ALEXA FLUOR 647 phalloidin | ThermoFisher Scientific, Inc. (Grand Island, NY) | A22287 |
| Prolong Gold with DAPI | ThermoFisher Scientific, Inc. (Grand Island, NY) | P36941 |
| Tetramethyl orthosilicate (TMOS), HCl, NaCl | Sigma-Aldrich | 87682-250ML, H1758-100ML, 53014-500G |
| Fetal bovine serum, 0.25% trypsin-EDTA, penicillin streptomycin | Gibco ThermoFisher | |
| 4% paraformaldehyde in PBS | Santa Cruz Biotechnology, Inc. (Dallas, TX) | CAS 30525-89-4 |
| 25% Glutaraldehyde | Electron Microscopy Sciences, Hatfield, PA | 16-220 |
| Aminopropyltriethoxysilane, | Gelest | SIA0610.1 |

Experimental Details

Mammalian Cell Culture

RAW 264.7 macrophage-like cells and ID8-OVA ovarian cancer cells were cultured at 37° C. in 5% $CO_2$ in the Dulbecco's Modified Eagle's Medium containing 10% fetal bovine serum, albumin, and penicillin/streptomycin (ThermoFisher Scientific, Grand Island, N.Y.). Bone marrow was harvested from the femurs of female murine C57BL/6 mice using a 27-gauge needle and syringe to flush the marrow from the bone. Cells were cultured for 8-10 days in RPMI 1640 medium (Life Technologies, Invitrogen, Carlsbad, Calif.) supplemented with 10% fetal bovine serum, 100 mM β-mercaptoethanol, penicillin/streptomycin, and 10 ng/ml recombinant murine granulocyte macrophage colony stimulating factor (GM-CSF). The resulting bone marrow dendritic cells (BMDC) were cultured with freshly prepared or dehydrated/rehydrated siloxane bacteria for 72 hours for antigen presentation studies.

Bacteria Culture

Bacterial strains used in this study included *Salmonella enterica* serovar *Typhimurium* LT2 (kind donation from Dr. Stanley Maloy, San Diego) and *E. coli* DH5-α expressing ovalbumin (Addgene Cambridge, Mass.). Both bacterial strains were typically cultured in Luria-Bertani (LB) growth medium and glycerol stocks prepared using LB medium containing 50% glycerol. To prepare bacteria samples for silicification, the following approaches were used. *Salmonella enterica* serovar *Typhimurium* LT2 was converted into a competent form using a Zymo kit (Zymo Research Corporation, Irvine, Calif.) and then transformed to express green fluorescent protein (GFP) using pGreen plasmid (Carolina Biological Supply Company, Burlington, N.C.) in the presence of ampicillin (100 μg/ml final). The newly generated ampicillin resistant GFP-*S. enterica* ser. *Typhimurium* LT2 was cultured overnight in ampicillin (100 μg/ml final) supplemented 40 ml LB medium at 37° C. in 250 ml PYREX flask (Corning Life Sciences, Tewksbury Mass.) shaking at 250 rpm. After two washes with 1×-PBS, samples were fixed with 2.5% glutaraldehyde (in 100 mM sodium cacodylate buffer) overnight at 4° C., washed three times with 1×-PBS and then used in the silicification process. Similarly, *E. coli* DH5-α expressing ovalbumin was cultured for 12 hours in 40 ml LB medium supplemented with ampicillin (100 μg/ml final), and then washed twice with 1×-PBS followed by fixation in 2.5% glutaraldehyde for overnight at 4° C., three washes with 1×-PBS and subsequent use in the silicification process. All the necessary protocols were followed in accordance with the safety guidelines.

Preparation of Silicified Bacteria and Pathogen Mimetic Cells

Fixed bacterial samples were rinsed twice with 154 mM NaCl (or 0.9% saline) and then suspended in a silicification solution containing 100 mM TMOS, 154 mM NaCl and 1.0 mM HCl (pH 3) in microcentrifuge tubes. The samples were rotated for three hours, 24 hours, or 72 hours at room temperature to allow silicification process to take place. To prepare dehydrated silicified bacteria, silicified bacterial samples were subjected to series of ethanol dehydration (30%, 50%, 70%, 90%, then 100% ethanol in water) for 10 minutes each and then dried under vacuum for 24 hours before storing the samples at room temperature for further use. Dry silicified bacteria were typically rehydrated for two hours using 1×-PBS before using them in cell-based assays.

ID8-OVA cells were fixed in 4% paraformaldehyde for 10 minutes or directly silicified by incubating in 100 mM tetramethyl orthosilicate (TMOS) in 1 mM HCl (pH 3) at room temperature for 24 hours. For aminosilane modification, silicified cells were dehydrated using ethanol and/or acetone and then dried under the vacuum. The dehydrated silicified cells were then incubated with aminopropyltriethoxysilane (APTES) or 2-aminoethyl-3-aminopropylmethyldimethoxysilane in 95% ethanol or acetone for 1-4 hours at room temperature to generate cells with different surface charges. Zeta potential measurements were obtained using a Malvern Nano-ZS Zetasizer using water as diluent. Cells were stored in water for variable times to determine stability of surface modifications. Adsorption of LPS-FITC to the cell surface was achieved by incubation of the modified cells with 50 μg/ml LPS-FITC in PBS at room temperature for 60 minutes. Cells were washed 1-3 times with PBS and fluorescence was measured using a microplate reader with excitation/emission at 488/510 nm.

Immunogenic Nanoparticles

DYLIGHT-488 (Thermo fisher Scientific, Inc., Waltham, Mass.)-conjugated immunogenic lipid coated mesoporous (ILM) nanoparticles were prepared as follows. A mixture of different lipids formulations, including monophosphoryl lipid A, in chloroform was prepared by mixing the corresponding lipids in a glass vial with total amounts ranging from 5 mg to 15 mg. The chloroform was removed from the lipid mixture under reduced pressure (rotator evaporator, 10 minutes) then kept under reduced pressure overnight in a vacuum pump in order to remove all chloroform residues. The lipid mixtures were then hydrated in PBS to 5 mg/mL and sonicated for at least 30 minutes at 45° C. A fresh solution of the model antigen ovalbumin (OVA) in bi-distilled water (1 mg/mL) was prepared before the loading procedure. Then, MSN (dye-labeled) in water (1 mg) were incubated (gentle shaking) in the OVA solution (with 1:1 or 1:5 MSN/OVA wt ratio) for 15 minutes at room temperature (22° C.) in the dark. Afterwards, on the OVA-MSN mixture, immunogenic liposomes (5 mg) were added under sonication (20 seconds). The obtained mixture was then centrifuged (21K rcf, 10 minutes, 4° C.) and the isolated pellet was suspended in PBS (10 mM) and centrifuged. The pellet was resuspended in PBS at 1 mg/mL before in vitro and/or in vivo experiments.

Confocal Microscopy Imaging

RAW macrophages were seeded onto glass cover slips in 6-well plates at a density of $5\times10^5$ cells per well. After a 24-hour incubation, siloxane *Salmonella typhimurium* bacteria were added in fresh complete media at variable ratios of bacteria to macrophages. LYSOTRACKER Red DND-99 (Molecular Probes, Inc., Eugene, Oreg.) (75 nM) was added to the cells in prewarmed culture media during the final 30 minutes incubation. BMDC were similarly seeded onto glass coverslips and incubated with fluorescent ILM nanoparticles or silicified ILM-treated ID8-OVA cells for one hour or two hours. After the final incubations, cells were washed with PBS, fixed with 4% paraformaldehyde in PBS for 15 minutes with prewarmed solutions followed by overnight refrigeration, rinsed twice with PBS, and permeabilized with 0.1% TRIRON-X (Thermo Fisher Scientific, Inc., Waltham, Mass.)_in PBS for 15 minutes with prewarmed solutions followed by overnight refrigeration, rinsed twice with PBS, and permeabilized with 0.1% TRIRON-X (Thermo Fisher Scientific, Inc., Waltham, Mass.) in PBS for minutes. Cells were then blocked with 1% BSA for 20 minutes and then labeled with 5 units/0.5 ml ALEXA FLUOR 647 phalloidin (Molecular Probes, Inc., Eugene, Oreg.) in 1% BSA for one hour. After rinsing with PBS, slides were mounted using mounting medium (VECTASHIELD antifade, Vector Laboratories, Inc., Newark, Calif. or PORLONG Gold, Thermo Fisher Scientific, Inc., Waltham, Mass.) with DAPI. Confocal images were acquired with a 63×/1.4 NA oil objective in sequential scanning mode using a Leica TCS SP8 confocal microscope.

Scanning Electron Microscopy (SEM) Imaging of Cells

RAW macrophages were seeded in 24-well plates containing 5×7 mm silicon chip specimen supports (Ted Pella, Inc., Redding, Calif.) at $1\times10^5$ cells per well. Cells were then incubated with a 10:1 ratio of siloxane *Salmonella typhimurium* bacteria to macrophage for one hour, as previously described. (Serda et al., *Biomaterials* 30:2440-2448, 2009). Cells were then fixed, washed in PBS, and dehydrated by sequential exposure to increasing concentrations of ethanol in water (30%, 50%, 70%, 90%, then 95% ethanol) followed by 100% ethanol twice, and 50:50 ethanol:HMDS for 10 minutes each. Cell were then placed in 100% HMDS for five minutes and air-dried overnight prior to sputter-coating with 5 nm gold-palladium. SEM images were acquired under high vacuum, at 20-30 kV, using an FEI Quanta 3D FEG, (FEI, Hillsboro, Oreg.). Some images have been pseudo-colored using ADOBE PHOTOSHOP (Adobe Systems Incorporated, San Jose, Calif.) and gamma levels adjusted to enhance image contrast and brightness.

The morphology of the bacterial samples was characterized using scanning electron microscope (SEM). Like the TEM, samples SEM imaging were prepared by drop casting approach. In brief, silicified bacteria samples were suspended in 200 proof ethanol, and then dropped onto 5×5 mm glass slides and allowed to dry. The glass slides were then mounted on SEM stubs (Ted Pella, Inc.) using conductive adhesive tape (12 mm OD PELCO Tabs, Ted Pella, Inc.). Samples were then sputter coated with a 10-nm layer of gold using a Plasma Sciences CrC-150 Sputtering System (Torr International, Inc.). SEM images were then acquired under high vacuum, at 10 kV, using an FEI Quanta series scanning electron microscope.

Transmission Electron Microscope (TEM) and Elemental Mapping

The morphology and elemental mapping of the bacterial samples were characterized using transmission electron microscope (TEM). TEM samples were prepared by drop casting method. In general, dehydrated fixed or silicified bacteria samples were suspended in 200 proof ethanol and then 5 μL of the suspension were dropped onto formvar carbon coated copper grids and then dried for 5-minutes at room temperature. Samples were then imaged using a JEOL 2010 FEG TEM/STEM microscope with Oxford EDS, Gatan Imaging Filter and EEL Spectrometer operating at 200 kV.

Inductively Coupled Plasma-Optical Emission Spectrometer (ICP-OES)

ICP-OES was used to measure the total Si concentration in the silicified bacteria samples. Dry silicified bacterial samples were mineralized in aqua regia (1:3 mixture of ultrapure $HNO_3$ and HCl) with a Digi prep MS SCP Science block digester at 95° C. for four hours. The digested samples were then diluted and passed through 0.45 μm filter. The concentration of Si was then measured using a PerkinElmer Optima 5300DV Inductively Coupled Plasma-Optical Emission Spectrometer (ICP-OES), with a detection limit of <0.5 mg/L. QA/QC measurements were also obtained to ensure quality results.

Flow Cytometry Analysis of Biomineralized Cell Uptake

RAW macrophages were seeded in six-well plates at $2.5\text{-}5\times10^5$ cells per well and allowed to adhere overnight. Cells were then incubated with bacteria for 24 hours for cell uptake studies. Cells were analyzed using a BD Fortessa or FACSCalibur flow cytometer using FACSDiva or CELL-QUEST software (BD Biosciences, Franklin Lakes, N.J.).

ALAMARBLUE (Trek Diagnostic Systems, Oakwood Village, Ohio) Proliferation Assay

Following a 24-hour incubation of RAW cells with bacteria at various ratios in a 96 well plate, ALAMARBLUE (Trek Diagnostic Systems, Oakwood Village, Ohio) was added at 10% of the volume per well. Following a one-hour incubation at 37° C., supernatant was transferred to a white 96-well plate and fluorescence read at 560/590 nm (excitation/emission).

Cytokine and ROS Analysis

Nitrite production by bacterial treated RAW cells was evaluated using a Greiss assay. Bacteria were added to the cell culture at the indicated ratio of bacteria to macrophage for 24 hours. The Greiss reagent was added to each well for 30 minutes and absorbance read at 548 nm. TNF-α secretion by RAW cells was measured in cell culture supernatants following a 24-hour incubation with bacteria using OptEIA™ ELISA kit (BD Biosciences, Franklin Lakes, N.J.)

Quantification and Statistical Analysis

Experimental groups were compared using unpaired, equal variance student's TTests.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A pharmaceutical composition comprising:
a silicified cell, a silicified cell-derived body, or a silicified vesicle; and
a pharmaceutically acceptable adjuvant.

2. The pharmaceutical composition of claim 1, wherein the cell is a silicified bacterial cell.

3. The pharmaceutical composition of claim 1, wherein the cell is a silicified tumor cell.

4. The pharmaceutical composition of claim 1, wherein the cell is part of a spheroid or organoid.

5. The pharmaceutical composition of claim 1, wherein the silicified cell comprises surface-modified siloxane.

6. The pharmaceutical composition of claim 5 wherein the surface-modified siloxane comprises a pathogen-associated molecular pattern (PAMP) or danger-associated molecular molecule (DAMP) adhered to the surface.

7. The pharmaceutical composition of claim 6 wherein the PAMP comprises lipopolysaccharide (LPS), monophosphoryl lipid A (MPL), CpG, or PolyIC.

8. The pharmaceutical composition of claim 5 wherein the surface-modified siloxane comprises a molecule that promotes internalization by antigen presenting cells.

9. The pharmaceutical composition of claim 8 wherein the molecule that promotes internalization by antigen presenting cells comprises calreticulin or CD47.

10. The pharmaceutical composition of claim 5 wherein the silicified cell is further modified with a secondary silane.

11. The pharmaceutical composition of claim 10 wherein the secondary silane tailors the cell surface for binding to distinct targeting or activation molecules.

12. The pharmaceutical composition of claim 10 wherein the secondary silane comprises aminosilane or carboxysilane.

13. A method of inducing an immune response against an antigen, the method comprising:
obtaining a cell that expresses the antigen;
silicifying the cell; and
administering to a subject a composition comprising:
the silicified cell; and
a pharmaceutically acceptable adjuvant, the composition administered in an amount effective to induce the subject to produce an immune response directed against the antigen.

14. The method of claim 13, wherein the silicified cell is a bacterium.

15. The method of claim 13, wherein the silicified cell is a tumor cell.

16. A method for treating a subject having, or at risk of having, a bacterial infection, the method comprising:
obtaining a bacterial cell that the subject is, or is at risk, of being infected by;
silicifying the bacterial cell; and
administering to the subject a composition comprising:
the silicified cell; and
a pharmaceutically acceptable adjuvant, the composition administered in an amount effective to ameliorate at least one symptom or clinical sign of infection by the bacterial cell.

17. The method of claim 16 wherein the bacterial cell is obtained from the subject.

18. A method for treating a subject having, or at risk of having, a tumor, the method comprising:
obtaining a tumor cell that the subject has or is at risk of having;
silicifying the tumor cell; and
administering to the subject a composition comprising:
the silicified tumor cell; and
a pharmaceutically acceptable adjuvant, the composition administered in an amount effective to ameliorate at least one symptom or clinical sign of having the tumor.

19. The method of claim 18 wherein the tumor cell is obtained from the subject.

20. The method of claim 19 wherein the tumor cell is obtained from fluid from the subject's peritoneal cavity.

* * * * *